(12) United States Patent
Hatanaka et al.

(10) Patent No.: US 7,304,744 B1
(45) Date of Patent: Dec. 4, 2007

(54) APPARATUS AND METHOD FOR MEASURING THE THICKNESS OF A THIN FILM VIA THE INTENSITY OF REFLECTED LIGHT

(75) Inventors: Masatsugu Hatanaka, Kashiwara (JP); Junichi Tanaka, Nara (JP); Toru Tanigawa, Ikoma (JP); Yasunobu Tagusa, Ikoma (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 09/471,829

(22) Filed: Dec. 23, 1999

(30) Foreign Application Priority Data

| Dec. 24, 1998 | (JP) | ................................. 10-367660 |
| Jul. 9, 1999 | (JP) | ................................. 11-195925 |
| Jul. 27, 1999 | (JP) | ................................. 11-211737 |

(51) Int. Cl.
*G01B 9/02* (2006.01)
*G01B 11/02* (2006.01)

(52) U.S. Cl. ...................................... 356/477; 356/504

(58) Field of Classification Search ................ 356/504, 356/503, 485, 630, 632, 477, 478, 492; 250/559.27, 250/559.28, 227.2, 227.21, 227.28, 227.19, 250/227.27

See application file for complete search history.

(56) References Cited

U.S. PATENT DOCUMENTS

| 4,697,926 | A | * | 10/1987 | Youngquist et al. ......... 356/478 |
| 4,787,749 | A | * | 11/1988 | Ban et al. .................... 356/632 |
| 5,223,914 | A | * | 6/1993 | Auda et al. .................. 356/630 |
| 5,844,239 | A | * | 12/1998 | Kimura ....................... 250/349 |
| 6,137,575 | A | * | 10/2000 | Sugiyama et al. ........... 356/503 |
| 6,139,797 | A | * | 10/2000 | Suzuki et al. ................ 356/445 |
| 2001/0052987 | A1 | * | 12/2001 | Kimba et al. ................ 356/630 |

FOREIGN PATENT DOCUMENTS

| JP | 40-10870 | 6/1965 |
| JP | 57-157105 | 9/1982 |
| JP | 61-165608 | 7/1986 |
| JP | 63-44106 | 2/1988 |
| JP | 4-172208 | 6/1992 |
| JP | 5-10726 | 1/1993 |
| JP | 5-323208 | 12/1993 |
| JP | 06-042923 | 2/1994 |
| JP | 06-201471 | 7/1994 |

(Continued)

OTHER PUBLICATIONS

Korean Patent Office Action (Notice of Ground of Rejection).

(Continued)

*Primary Examiner*—Patrick Connolly
(74) *Attorney, Agent, or Firm*—David G. Conlin; Steven M. Jensen; Edwards Angell Palmer & Dodge LLP

(57) ABSTRACT

A thin film thickness measurement apparatus that can measure immediately after film growth thickness of a thin film of a substrate that is grown includes a light receiving/projecting unit directing light substantially perpendicular to the substrate and receiving light reflected from the substrate, and an analyze unit analyzing thickness of a thin film of the substrate according to intensity of reflected light received by the light receiving/projecting unit.

12 Claims, 24 Drawing Sheets

FOREIGN PATENT DOCUMENTS

| | | |
|---|---|---|
| JP | 7-071924 | 3/1995 |
| JP | 7-294220 | 11/1995 |
| JP | 7-302826 | 11/1995 |
| JP | 08136710 A | 5/1996 |
| JP | 08-301433 | 11/1996 |
| JP | 9-118600 | 5/1997 |
| JP | 10-154221 | 6/1998 |
| JP | 10-154693 | 6/1998 |
| JP | 11-014312 | 1/1999 |
| JP | 11-160030 | 6/1999 |
| JP | 11184104 A | 7/1999 |
| JP | 2000-352505 | 12/2000 |

OTHER PUBLICATIONS

Office Action and English language translation of the Office Action. The Office Action was mailed on Sep. 28, 2004 in connection with the counterpart Japanese Patent Application No. H11-195925.

Japanese Patent Office Action mailed Mar. 22, 2005 and English Translation.

Korean Patent Office Action (Notice of ground of Rejection) 2005.

Korean Patent Office Action (Notice Of Ground Of Rejection).

* cited by examiner

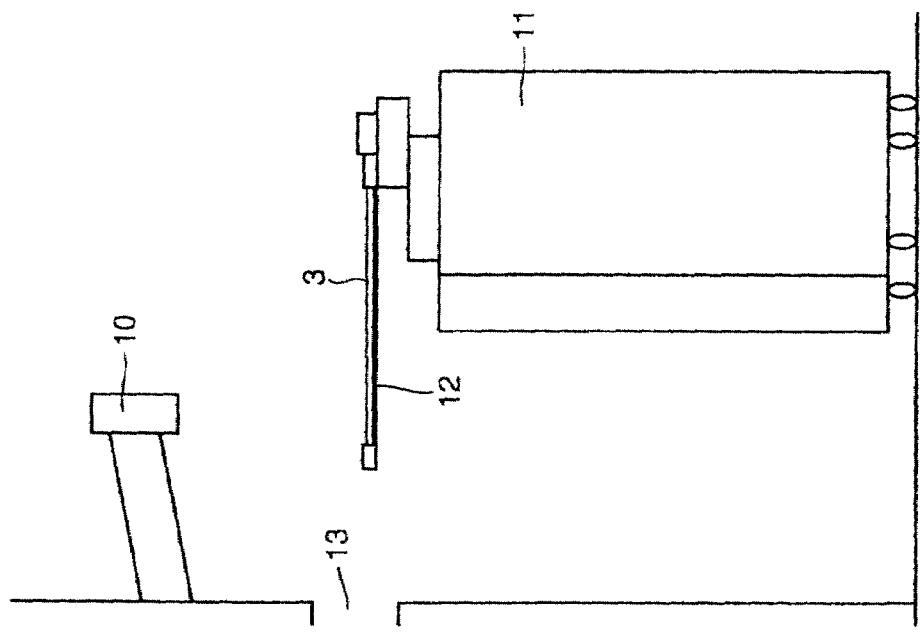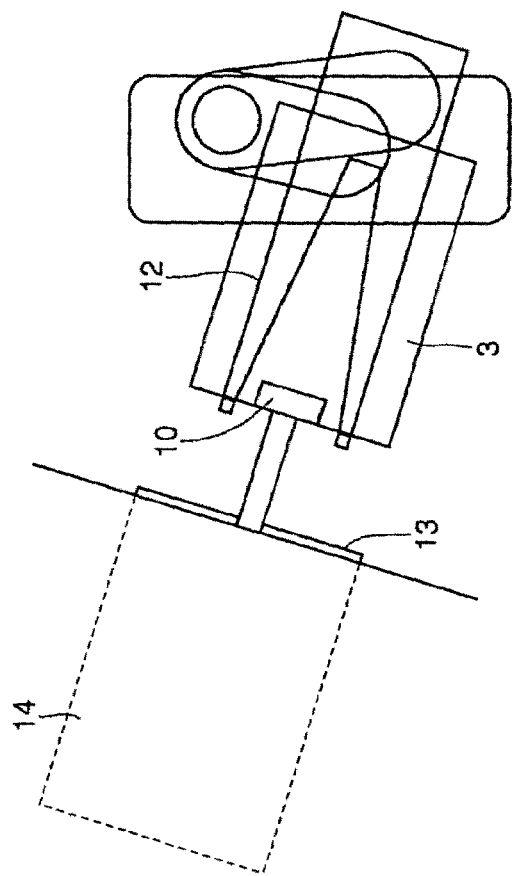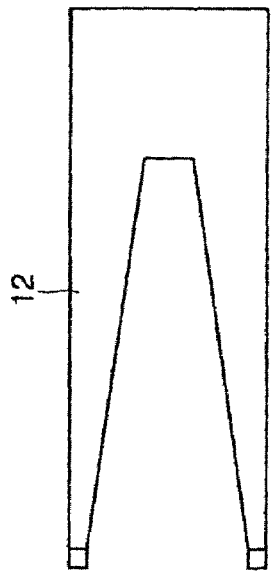
FIG.13A
FIG.13B
FIG.13C

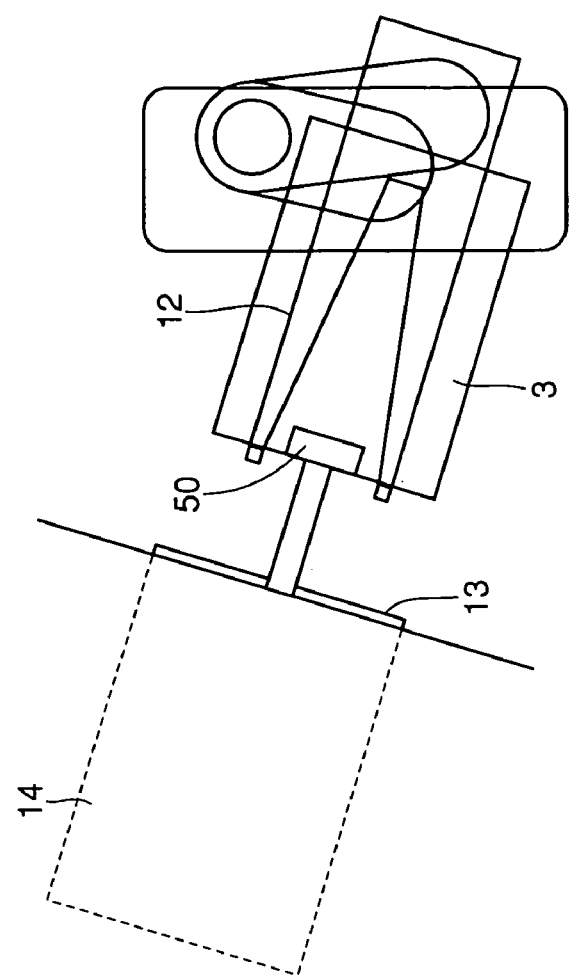
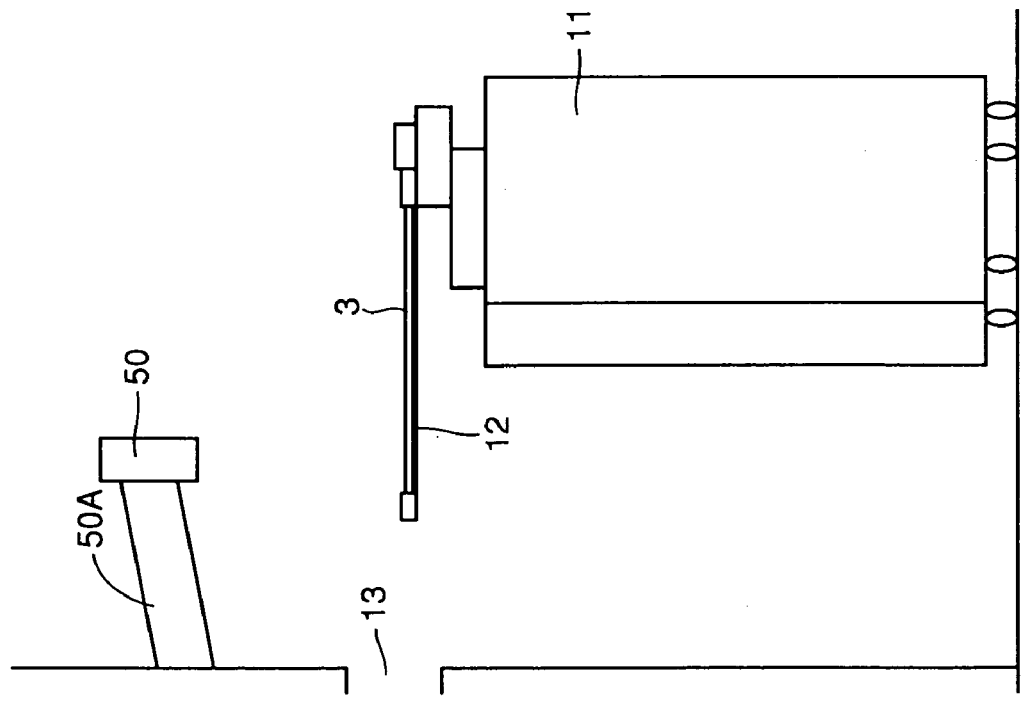
FIG.20A
FIG.20B

SUBSTRATE

APPARATUS AND METHOD FOR MEASURING THE THICKNESS OF A THIN FILM VIA THE INTENSITY OF REFLECTED LIGHT

BACKGROUND OF THE INVENTION

1. Field of the Invention

The present invention relates to a film thickness measurement apparatus of a thin film, and an electronic component fabrication apparatus including a film growth step. Particularly, the present invention relates to a thickness measurement apparatus measuring the thickness of various thin films formed on a substrate using the light interference method, and an electronic component fabrication apparatus.

2. Description of the Background Art

In the fabrication of electronic components such as of semiconductor devices and liquid crystal display devices, film growth technique such as plasma processing and sputtering is now widely used. By detecting various properties of a thin film formed by the film growth technique, various parameters for forming a thin film can be obtained. Also, various deficiencies during film growth can be promptly detected.

The thickness of a thin film greatly affects the pattern formation in thin films as well as to the properties such as conductivity and insulation thereof. Erroneous film thickness may cause disconnection and shorting in interconnection films and the like formed above the thin film. The film thickness is an important control factor that greatly influences the fabrication yield and reliability.

Conventionally, measurement of thickness of a thin film formed by a film growth apparatus is time consuming. Critical transportation and handling of the substrate are required so that the thin film is not damaged during thickness measurement. Accordingly, the measurement apparatus becomes so complex that it is difficult to introduce the measurement apparatus into an empty space of an existing line. In most cases, measurement was carried out off-line. The method of measuring the thickness of a thin film includes various methods such as the contact type method measuring a stepped portion in the thin film or using an ellipsometer.

Referring to FIG. 1, a film thickness measurement apparatus using an ellipsometer includes a polarizer 101 and an analyser 102. The light from a light source is polarized by polarizer 101 to be directed onto a thin film formation substrate 103 that is to be worked. Light reflected from substrate 103 is received by analyser 102 to have the polarized status of the reflected light detected by a detector. The detector compares the polarized status of incident light with that of the reflected light to obtain the optical constant (refractive index, attenuation coefficient) of the film thickness.

When a thin film layer 104 is formed on a substrate 106 covering a wiring pattern 105 of metal and the like as shown in FIG. 2, subtle unevenness is exhibited at that portion. Therefore, the film thickness could not be measured by the above-mentioned measurement method.

Thus, a particular region absent of wiring pattern 105 is selected and film growth effected thereon. Alternatively, a film is grown on a dummy substrate absent of wiring pattern, and the film thickness of an arbitrary point of that thin film is measured. Film growth conditions are determined to eliminate any deficiency in the thin film on the dummy substrate. Then, those film growth conditions are applied in the actual stage of production. Fabrication is effected on the assumption that a similar film is grown.

A method utilizing light interference is known as the measurement method relatively impervious to the unevenness on the substrate. This light interference method measures the thickness of a thin film by analyzing the spectrum of light reflected from or passing through the substrate.

An example of a light interference method will be described with the reference to FIG. 3. Light emitted from a light source is reflected from a substrate 103. The light reflected at the surface side of substrate 103 is a combination of light R1 reflected from the surface of thin film 104 and light R2 reflected from the surface of the main body 106 of substrate 103 excluding thin film 104.

The relationship between the wavelength and light intensity of the reflected light of FIG. 3 detected by a spectroscope will be described with reference to FIG. 4. The wavelength of the reflected light is plotted along the abscissa and light intensity is plotted along the ordinate in the graph. Light R1 and R2 interfere with each other, so that the light intensity becomes strong and weak with respect to the wavelength of the reflected light. This light interference occurs due to the difference in the light paths of light R1 and R2. Therefore, light interference depends on the thickness of thin film 104 and the angle of light radiation. The curve of the wavelength-light intensity in the graph is altered according to the thickness of thin film 104. Therefore, the thickness of film 104 can be obtained by analyzing the shape of the curve of the wavelength-light intensity in the graph depending upon the condition.

The peak valley method is known as the analyzing method of the curve of the wavelength-light intensity shown in FIG. 4. The wavelength corresponding to the peak in light intensity (points a and b in FIG. 4) in the wavelength-light intensity relationship curve is obtained. The film thickness is obtained from a relationship equation thereof.

As a film thickness measurement method using the wavelength-light intensity relationship curve, Japanese Patent Laying-Open No. 5-10726 discloses an invention of the film thickness measurement method utilizing transmitted light. In this measurement method, the curve of the relationship between the wavelength and light intensity of light transmitted through a transmittive substrate is obtained using a light source and a sensor. In addition to the peak valley method that obtains the wavelength corresponding to light intensity of the maximum level, a method is known of measuring the film thickness by altering the thickness and refractive index of the thin film so that the relationship curve approximates the wavelength-light intensity logic relationship curve as much as possible obtained from logic expressions that will be described afterwards. The following relationship is established where T is the transmittance of the thin film, $n'$ is the refractive index of the thin film, $n'_0$ is the refractive index of air, $n'_1$ is the refractive index of the transparent substrate, $r_0$ is the amplitude reflectance when light enters the thin film from air, $r_1$ is the amplitude reflectance when light enters the transparent substrate from the thin film, $\delta$ is the offset in phase when light travels through the thin film, $\delta_0$ is the offset in phase when light enters the thin film from air, and $\delta_1$ is the offset in phase when light enters the transparent substrate from the thin film.

$$T = \frac{4 \times n'^2 \times (n'_0 + n'_1)^2}{(n' + n'_0)^2 \times (n' + n'_1)^2} \times \frac{1}{1 + r_0 \times r_1 + 2 \times r_0 \times r_1 \times \cos(\delta + \delta_0 + \delta_1)} \quad (1)$$

Since phase offset δ when light passes through the thin film depends upon thickness d the thin film and light wavelength λ, the relationship between wavelength λ and thin film transmittance T can be obtained from equation (1). Therefore, thin film thickness d and thin film refractive index n' are altered, and values thereof corresponding to the case where the wavelength-light intensity logic relationship curve obtained from equation (1) is closest to the wavelength-light intensity measured relationship curve are taken as the measurement values.

In the film thickness measurement apparatus employing an ellipsometer of FIG. 1, the position relationship of substrate 103 with respect to polarizer 101 and analyser 102 must be fixed. The thickness of the thin film cannot be measured when there is vertical oscillation, inclination, shifting and the like in substrate 103. Particularly in the fabrication line of a liquid crystal display device using a thin film glass substrate of approximately 0.5–1.1 mm in thickness and of a large size at least several hundred mm square, significant warping(partial inclination), oscillation, and like occur in the substrate. In order to use the film thickness measurement apparatus in-line, a robust large stage must be installed to be impervious to any partial inclination and oscillation. It is also necessary to mount polarizer 101, analyser 102 and substrate 103 in precise position to set the optical axis. Thus, it is difficult to measure a plurality of sites on substrate 103 simultaneously. Also, the film thickness measurement apparatus cannot be introduced in a limited space in-line since the measurement system is of a large scale in many cases.

In the method where a film is grown on a dummy substrate that is absent of a wiring pattern and measuring the film thickness of an arbitrary point of that thin film, there is a problem that the substrate of the product is not always identical to that of the dummy substrate even if optimum growth conditions are obtained by the dummy substrate and employed for the actual stage of production.

Furthermore, the extra step of carrying out film growth on a dummy substrate is required. This means that the number of steps required in the film thickness measurement process is increased. It may become necessary to reduce the number of measurement sites of film thickness for one product. The possibility of not detecting improper film thickness or delay in detecting improper film thickness may occur to result in significant damage.

Microscopic patterns of wiring and other metal films are formed between the substrate and the thin film in various electronic components. The above-described peak-valley method which is a light interference method is employed as the film thickness measurement method to have such influences relatively reduced. However, the peak valley method is disadvantageous in that thin film thickness measurement cannot be implemented in logic if there is only one peak or valley in the measured wavelength range, as shown in FIG. 5. Even if there are two or more peaks or valleys of light intensity, the peak position of light intensity will be shifted when light absorption by the thin film occurs in the wavelength range near the peak or the valley. Therefore, proper measurement of the film thickness cannot be obtained.

The film thickness measurement method disclosed in Japanese Patent Laying-Open No. 5-10726 analyzes the waveform per se of the wavelength-light intensity curve. Therefore, thickness of the thin film can be measured even if there is only one peak or valley of the light intensity. However, this measurement method does not take into account the absorption coefficient of the thin film, as apparent from equation (1). In the case where there is light absorption by the thin film in the measuring wavelength range, the wavelength range of measurement must be shifted to a wavelength range absent of absorption by the thin film. This means that many light sources differing in wavelength range must be prepared in the case of measuring a plurality of thin films. A mechanism to switch the light source according to the type of the thin film to be measured is required. Accordingly, the thin film measurement apparatus is increased in size and cost.

In the case where a multilayer film is grown on a substrate, the logic curve can be obtained by application of equation (1) in principle. However, a long period of time is required to obtain a curve that matches the actually measured wavelength-light intensity curve by altering all the parameters since the number of parameters increases in proportion to the number of the thin films. In the logic expression obtaining the thickness of a multi layer film, the total sum of the error of the thickness of each thin film will correspond to the error of the film thickness of the multilayer film. Thus, there is a problem that the logic curve does not easily match the actual measured curve.

Film thickness measurement is time consuming because light radiation of a large wavelength range and analysis thereof are required. Since only a transmittive type substrate is expected as the subject, there is also the problem that thin film measurement is difficult or the measured accuracy degraded in the case where the substrate is not transparent or when there is a light blocking film such as wiring between the thin film and the substrate.

It is noted that the position relationship of the substrate, the light source and the sensor must be fixed. The light path may be oscillated when the substrate is shifted vertically, inclined or oscillated. It was difficult to properly measure the film thickness. Particularly in the fabrication line of a liquid crystal display device using a thin film glass substrate of approximately 0.5–1.1 mm in thickness and of a large size at least several hundred mm square, significant warping (partial inclination), oscillation, and like occur in the substrate. In order to use the film thickness measurement apparatus in-line, a robust large stage must be installed to be impervious to any partial inclination and oscillation. Thus, the film thickness measurement apparatus is increased in size. Furthermore, the substrate and the sensor must be positioned accurately to set the optical axis. Therefore, it is difficult to measure a plurality of sites on a substrate simultaneously. Also, the sensor cannot be introduced in a limited space of the existing line in many cases.

A possible consideration is that the film thickness of a plurality of sites is to be measured while moving the sensor. However, it is difficult to move the sensor at high speed while maintaining the optical axis at high accuracy. This means that the measurement is time consuming.

It was difficult to measure the film thickness in-line by the conventional film thickness measurement methods. An overall or local defect in the substrate could be detected in the stage of inspection after several processing steps have already been carried out. There is a time lag from the occurrence of a defect until the defect is detected. Thus, there was a problem that a large amount of defective products will be generated during the time lag.

In the conventional film thickness measurement method, the breakdown or time for maintenance of the film thickness measurement apparatus could not be predicted due to change in various conditions such as degradation of the light source of the film thickness measurement apparatus. This is one cause of degrading the operating efficiency of the film thickness measurement apparatus.

In the invention disclosed in Japanese Patent Laying-Open No. 5–10726, a light source and a sensor are installed at both sides of the substrate since the measurement method employs transmitted light. In the case where the distance between the substrate and the light source or sensor is too small when the apparatus is employed in-line, the substrate will be brought into contact with the light source or the sensor due to oscillation or position shifting of the substrate to result in breakage or damage of the substrate.

Furthermore, thin film measurement utilizing transmitted light has the disadvantage that measurement is difficult since light is not easily transmitted in the region of the substrate where a reflective film is formed at a constant area ratio.

Furthermore, when thin films of a multilayer are formed on the substrate, each thin film cannot be calculated accurately unless the absorption coefficient of respective thin films are taken into account. There is a complicated distribution of reflected light and refracted light when a patterned reflective film that is concave and convex at a constant area ratio on the substrate is present, or when light is reflected and refracted at respective interfaces of the multilayer films. There was a problem that the distribution of the transmitted light becomes complex, whereby measurement of the thickness of the thin film becomes difficult.

SUMMARY OF THE INVENTION

In view of the foregoing, an object the present invention is to provide a thin film thickness measurement apparatus and method that can measure the thickness of a grown thin film of a substrate immediately after film growth.

Another object of the present invention is to provide a thin film thickness measurement apparatus and method reduced in constraint of installation of existing film growth apparatus.

A further object of the present invention is to provide a thin film thickness measurement apparatus and method that allows measurement of thickness of the thin film at high accuracy and in a short time.

Still another object of the present invention is to provide a thin film thickness measurement apparatus that can measure the thickness of a thin film independent of the type and structure of the thin film.

A still further object of the present invention is to provide a thin film thickness measurement apparatus that can measure the film thickness of a thin film at high accuracy even if there is a portion in which a reflective film is formed at a constant area ratio on the substrate.

Yet a further object of the present invention is to provide a thin film thickness measurement apparatus that can measure the thickness of a thin film of each layer at high accuracy even in the case where thin films of a multilayer are formed on the substrate.

Yet another object of the present invention is to provide an electronic component fabrication apparatus and method that can suppress generation of a defective product to the minimum even when defective products are generated.

Yet a still further object of the present invention is to provide an electronic component fabrication apparatus and method that allows film thickness measurement at high speed without degrading the production rate.

An additional object of the present invention is to provide an electronic component fabrication apparatus and method that allows film thickness measurement at high accuracy.

Yet an additional object of the present invention is to provide an electronic component fabrication apparatus predicting breakdown or maintenance time of a thin film thickness measurement apparatus to improve the operating efficiency of the thin film thickness measurement apparatus.

Yet a still additional object of the present invention is to provide an electronic component fabrication method that can reduce the size of the thin film thickness measurement apparatus and that allows film thickness measurement in-line.

According to an aspect of the present invention, a thin film thickness measurement apparatus includes a light receiving unit directing light substantially perpendicular to a substrate and receiving light reflected from the substrate, and an analyze unit analyzing the thickness of a thin film of a substrate according to intensity of reflected light received at the light receiving unit.

The light receiving unit is relatively impervious to the vertical shift, inclination, oscillation and the like of the substrate since light is directed substantially perpendicular to the substrate and the light reflected from the substrate is received.

Preferably, the light receiving unit includes a light source, and an optical fiber guiding light from the light source onto the substrate, and receiving light reflected from the substrate to guide the reflected light to the analyze unit.

Since the light receiving unit can be formed by only a light source and an optical fiber, the structure of the thin film thickness measurement apparatus can be simplified.

Further preferably, the analyze unit includes a spectroscope to divide light reflected from the substrate according to intensity of each wavelength, and a calculation unit to calculate the thickness of the thin film of the substrate according to the intensity of each divided wavelength.

The calculation unit can provide calculation of the film thickness in a short time since the thickness of the thin film of the substrate is calculated according to the intensity of each wavelength divided by the spectroscope.

Further preferably, the light receiving unit directs light substantially perpendicular to the substrate placed on a robot hand.

Since the light receiving unit directs light substantially perpendicular to the substrate placed on the robot hand, the existing robot for substrate transportation can be used.

Further preferably, the light receiving unit is placed in the proximity of the outlet of a gate valve of a film growth apparatus.

This provides the advantage that the film thickness can be measured using the existing film growth apparatus.

According to another aspect of the present invention, a thin film thickness measurement method includes the steps of directing light substantially perpendicular to a substrate and receiving light reflected from the substrate, and analyzing the thickness of a thin film of the substrate according to the intensity of the received reflected light.

Accordingly, influence of vertical deviation, inclination, oscillation and the like of the substrate is suppressed.

Preferably, the step of measuring the thickness of a thin film includes the steps of analyzing the reflected light from the substrate according to intensity of each wavelength, and calculating the thickness of the thin film of the substrate according to the intensity of each divided wavelength.

This provides the advantage that the film thickness can be calculated in a short time.

According to a further aspect of the present invention, a thin film thickness measurement apparatus includes a light source having a wavelength range of at least approximately 220 nm to 850 nm, a projection unit guiding light from the light source and directing the light to a thin film formed on a substrate, a light receiving unit receiving light reflected from the thin film or the substrate, a spectroscope dividing reflected light received at the light receiving unit for each wavelength, and a calculation unit calculating the thickness of the thin film according to intensity of reflected light in the wavelength range of approximately 220 nm to 850 nm divided by the spectroscope.

The thickness of the thin film is measured utilizing reflected light at the interface portion of the thin film. Thin film thickness measurement can be effected even if the substrate is transparent such as glass or opaque. Therefore thin film thickness measurement can be effected with respect to a wide range of products. The film thickness can be measured for the reflected light intensity of a wavelength range from at least approximately 220 nm to 850 nm. Therefore, film thickness measurement is allowed with two lamps (halogen lamp and deuterium lamp) at most. By the analysis of the reflected light intensity in the wavelength range of at least approximately 220 nm to 850 nm, thickness measurement of most of single layer films such as an ITO (Indium Tin Oxide), silicon nitride film, amorphous silicon film and n$^+$ type amorphous silicon film as well as a multilayer formed of those films generally employed in many of the electronic components of liquid crystal displays, semiconductor devices, image sensors, and the like can be measured. Thus, thin film thickness measurement can be carried out regardless of the type and structure of the thin film.

Preferably, the projection unit includes an optical fiber that guides light from the light source and directs the light to the thin film formed on the substrate. The light receiving unit includes an optical fiber receiving reflected light from the substrate and guiding the received reflected light to the spectroscope.

The projection unit and the light receiving unit can be formed exclusively of optical fibers. Therefore, the thin film thickness measurement apparatus can be reduced in size. The thin film thickness measurement apparatus can be easily introduced into an existing or new line in the empty space.

Further preferably, the light source includes a plurality of lamps of different wavelength ranges provided in the same casing.

By providing a plurality of lamps in the same casing, switching of light directed to the substrate becomes more simple than the case where lamps are provided in separate casings. The structure of the projection unit that guides light from the light source can be simplified. Accordingly, the thin film thickness measurement apparatus can be reduced in size.

Further preferably, the plurality of lamps can be lit independently.

The combination of the lamps turned on can be altered to direct light of various wavelength ranges to the thin film. Thin film thickness measurement can be carried out appropriately by selecting light of an appropriate wavelength range corresponding to the material of the thin film.

Further preferably, the projection unit is arranged at a position directing light substantially perpendicular to the substrate. The light receiving unit is arranged at a position receiving light reflected substantially perpendicular from the substrate.

By providing the projection unit and the light receiving unit substantially perpendicular to the substrate, the projection unit and the light receiving unit can be provided as a unitary element and introduced into an empty space in the existing line. Since the incident angle of light is substantially perpendicular, deviation in the light path of the reflected light is reduced. Thin film thickness measurement is allowed impervious to oscillation or inclination of the substrate and the distance of the substrate to the projection unit or the light receiving unit.

Further preferably, the projection unit includes one optical fiber guiding light from the light source to direct light substantially perpendicular to the thin film formed on the substrate. The light receiving unit includes a plurality of optical fibers arranged around an optical fiber, each receiving light reflected from the substrate.

Light is projected symmetrically about the axis even if the substrate is inclining, so that the reflected light is received by any of the plurality of optical fibers. Thin film thickness measurement can be carried out irrespective to the inclination of the substrate.

Further preferably, the light receiving unit includes one optical fiber arranged at a position receiving light reflected substantially perpendicular from the substrate. The projection unit includes a plurality of optical fibers arranged around an optical fiber to guide the light from the light source and directing the light substantially perpendicular to the thin film formed on the substrate.

Any of the reflected light from the light directed by the plurality of optical fibers symmetrically about the axis can be received by one optical fiber located at the center of the plurality of optical fibers even if the substrate is inclined. Therefore, thin film thickness measurement can be carried out irrespective of whether the substrate is inclined or not.

Further preferably, the calculation unit calculates the film thickness d of a thin film by the following equations (2)–(7) where $n_0$ is the refractive index of the substrate, $n_1$ is the refractive index of the thin film, $n_2$ is the refractive index of air, $\lambda$ is the light wavelength, $k$ is the absorption coefficient of the thin film, and $R$ is the light reflectance intensity at wavelength $\lambda$, according to the intensity of reflected light divided by the spectroscope.

$$R = \frac{R(2,1) + R(1,0) \times k^2 + 2 \times \rho(2,1) \times \rho(1,0) \times k \times \cos(\gamma)}{1 + R(2,1) + R(1,0) \times k^2 + 2 \times \rho(2,1) \times \rho(1,0) \times k \times \cos(\gamma)} \quad (2)$$

$$\rho(2,1) = \frac{n_1 - n_2}{n_1 + n_2} \quad (3)$$

$$\rho(1,0) = \frac{n_0 - n_1}{n_0 + n_1} \quad (4)$$

$$R(2,1) = \rho(2,1)^2 \quad (5)$$

$$R(1,0) = \rho(1,0)^2 \quad (6)$$

$$\gamma = 4\pi n_1 d/\lambda \quad (7)$$

Equation (2) takes into account the absorption coefficient k of the thin film. Therefore, thin film thickness measurement is allowed even with respect to a wavelength range in which light is absorbed. Film thickness measurement is allowed at high accuracy and in a short time without having to restrict the wavelength range of the light source. Usage in-line is allowed without degrading the line production rate.

Further preferably, the calculation unit calculates the film thickness d(p) of the p-th layer of thin film by the following equations (8)–(18), where $n_0$ is the refractive index of the substrate, n(p) is the refractive index of the p-th layer of thin film from the substrate, n(p+1) is the refractive index of air, $\lambda$ is the light wavelength, and k(p) is the absorption coefficient of the p-th layer of thin film, according to the intensity of reflected light divided by the spectroscope.

$$R(p+1, 0) = \frac{G+H}{1+J+H} \quad (8)$$

$$G = R(p+1,p) + R(p,0) \times k(p)^2 \quad (9)$$

$$H = 2 \times \rho(p+1,p) \times \sqrt{R(p,0)} \times k(p) \times \cos(\gamma(p,0) + \gamma(p)) \quad (10)$$

$$J = R(p+1,p) \times R(p,0) \times k(p)^2 \quad (11)$$

$$\rho(p+1, p) = \frac{n(p) - n(p+1)}{n(p) + n(p+1)} \quad (12)$$

$$R(p+1,p) = \rho(p+1,p)^2 \quad (13)$$

$$\tan\gamma(p, 0) = \frac{D}{E+F} \quad (14)$$

$$D = \sqrt{R(p-1,0)} \times (1 - \rho(p,p-1)^2) \times \sin(\gamma(p-1,0) + \gamma(p-1)) \quad (15)$$

$$E = \gamma(p,p-1) \times (1 + R(p-1,0)) \quad (16)$$

$$F = \sqrt{R(p-1,0)} \times (1 + \rho(p,p-1)^2) \times \cos(\gamma(p-1,0) + \gamma(p-1)) \quad (17)$$

$$\gamma(p) = 4\pi n(p) d(p) \cos\theta(p)/\lambda \quad (18)$$

Equation (8) takes into account the absorption coefficient k(p) of each layer of the thin film. Therefore, thin film thickness measurement is allowed for a multilayer film even with respect to a wavelength range in which light is absorbed. Thickness measurement can be carried out at high accuracy and in a short time without limiting the wavelength range of the light source. Usage in-line is allowed without degrading the line production rate.

Further preferably, the thin film includes a transparent conductive film. The substrate has a coat of a reflective film.

By providing a reflective film under the thin film that is to be measured, the thin film can be measured accurately even if there is an underlying thin film having a refractive index approximating that of the thin film that is to be measured.

Further preferably, the reflective film has an area greater than 0% and not more 50% the area of the region that is to be measured. The calculation unit calculates the thickness of the thin film ignoring reflectance at the reflective film.

The inventors of the present invention have confirmed by experiments that thin film thickness measurement can be carried out correctly on the assumption that the entire layer under the target layer is a transparent substrate such as a glass substrate.

Further preferably, the reflective film has an area 50–100% the area of the region of the film that is to be measured. The calculation unit measures the thickness of the thin film ignoring influence of light transmittance towards the underlying layer of thin film.

The inventors of the present invention have confirmed by experiment that thin film thickness measurement can be carried out accurately, when the target layer is a transparent conductive film such as an ITO film and a reflective film of Ta is formed under the ITO layer on the assumption that there is a uniform reflective film under the ITO layer.

Further preferably, the reflective film is a metal film or an alloy film with tantalum, titanium, aluminum, chromium or molybdenum as the main component.

These materials are those typically used in semiconductor devices and liquid crystal displays. Therefore, extra material or processing step to additionally form a reflective film is not required by using a layer underlying the target thin film as a reflective film.

According to still another aspect of the present invention, an electronic component fabrication apparatus includes a film growth apparatus and a thin film thickness measurement apparatus. The thin film thickness measurement apparatus includes a light source, a projection unit guiding light from a light source and directing the light substantially perpendicular to a thin film formed on a substrate, a light receiving unit receiving light reflected from the thin film or the substrate, a spectroscope dispersing reflected light received at the light reflecting unit for each wavelength, and a calculation unit calculating the thickness of the thin film according to intensity of reflected light dispersed at the spectroscope. The thin film thickness measurement apparatus is provided in the fabrication line of electronic components, and at a position that carries out thin film thickness measurement right after a film is grown by the film growth apparatus.

By providing the projection unit and the light receiving unit substantially perpendicular to the substrate, the projection unit and the light receiving unit can be provided as a unitary element to be introduced into an empty space in the existing line. Since the incident angle of light is substantially at right angles, deviation in the light path of the reflected light is reduced. Therefore, thin film thickness measurement is allowed impervious to oscillation or inclination of the substrate and to the distance of the substrate to the projection unit or the light receiving unit.

Since measurement is carried out immediately after the film is grown by the film growth apparatus, defect in the grown film can be immediately detected. Thus, generation of defective products can be suppressed to the minimum.

Preferably, the projection unit includes a plurality of projection units directing light guided from the light source to a plurality of sites on the substrate at the same time. The light receiving unit includes a plurality of light receiving units receiving light reflected from the plurality of sites.

Variation in the film thickness in the substrate is great in the case of substrates of large size employed in liquid crystal displays. There may be the case where deficiency in the grown film occurs locally by abnormal discharge and the like during the film growth step. By arranging a plurality of the projection units and light receiving units, the film thickness measurement of a plurality of sites can be carried out simultaneously. Therefore, local film thickness defect can be detected without degrading the production rate.

Further preferably, the thin film thickness measurement apparatus includes a plurality of first connectors attached at the leading ends of the plurality of light receiving units, respectively, and a second connector having one end connected to the spectroscope and the other end connected to any of the plurality of first connectors to guide the light from the connected first connector to the spectroscope.

The light guided to the spectroscope is switched according to the combination of the first connector and the second connector. Usage of connectors to switch the light provides the advantage that light leakage is prevented to increase the light usage efficiency than the case where a shutter is used. Therefore, the accuracy of thin film measurement can be improved.

Further preferably, the thin film thickness measurement apparatus further includes a reflectance calibration projection unit guiding light from the light source and directing the light substantially perpendicular to light reflective material, a reflectance calibration light receiving unit receiving light reflected from the reflective material, and a reflectance calibration unit calibrating a parameter used in calculating thin film thickness by the calculation unit according to light received at the reflectance calibration light receiving unit.

The parameter used in calculating the thin film thickness is calibrated using reflected light from the reflective material. Therefore, thin film thickness measurement is carried out while calibrating the parameter even during the fabrication of electronic components. Therefore, the accuracy of thin film thickness measurement can be improved.

Further preferably, the thin film thickness measurement apparatus includes a light source calibration projection unit guiding light from the light source and directing the light to light reflective material, a light source calibration light receiving unit receiving light reflected from the reflective material, and a light source amount reduction detection unit detecting reduction of the light amount of the light source according to light received at the light source calibration light receiving unit.

Reduction in the amount of light of the light source is detected using reflected light from the reflective material. Accordingly, the lifetime of the light source can be identified, so that the light source can be exchanged prior to the lifetime. The operating efficiency of the thin film thickness measurement apparatus can be improved by carrying out replacement of the light source during the film growth stage or the when the line is at stop.

Further preferably, the thin film thickness measurement apparatus further includes a disturbance light receiving unit receiving disturbance light, and a disturbance light calibration unit calibrating a parameter used in calculating thin film thickness in the calculation unit according to light received at the disturbance light receiving unit.

The parameter used in calculating the thickness of the thin film is calibrated using the disturbance light. Therefore, thin film thickness measurement is carried out impervious to the disturbance light. Therefore, accuracy of thin film measurement can be improved.

According to yet a further aspect of the present invention, an electronic component fabrication method includes the steps of growing a thin film on a substrate, directing light substantially perpendicular to the thin film formed on the substrate right after film growth, receiving light reflected from the thin film or the substrate, dispersing the received reflected light for each wavelength, and calculating the thickness of the thin film according to the intensity of the reflected light dispersed.

Thin film thickness measurement is carried out immediately after film growth. Therefore, defect in the grown film can be detected promptly to suppress generation of defective products at the minimum.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 13A–13B show an example of installment of the thin film thickness measurement apparatus of the first embodiment.

FIG. 13C shows the configuration of a robot hand.

FIGS. 20A and 20B show examples of installation of the thin film thickness measurement apparatus of the second embodiment.

DESCRIPTION OF THE PREFERRED EMBODIMENTS

First Embodiment

Figure 1:
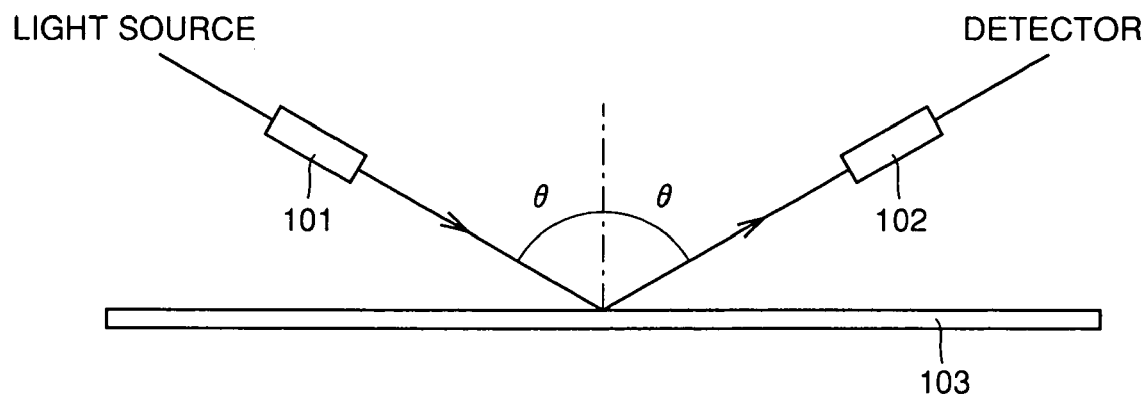
FIG. 1 is a diagram to describe a film thickness measurement method using a conventional ellipsometer.
Figure 2:
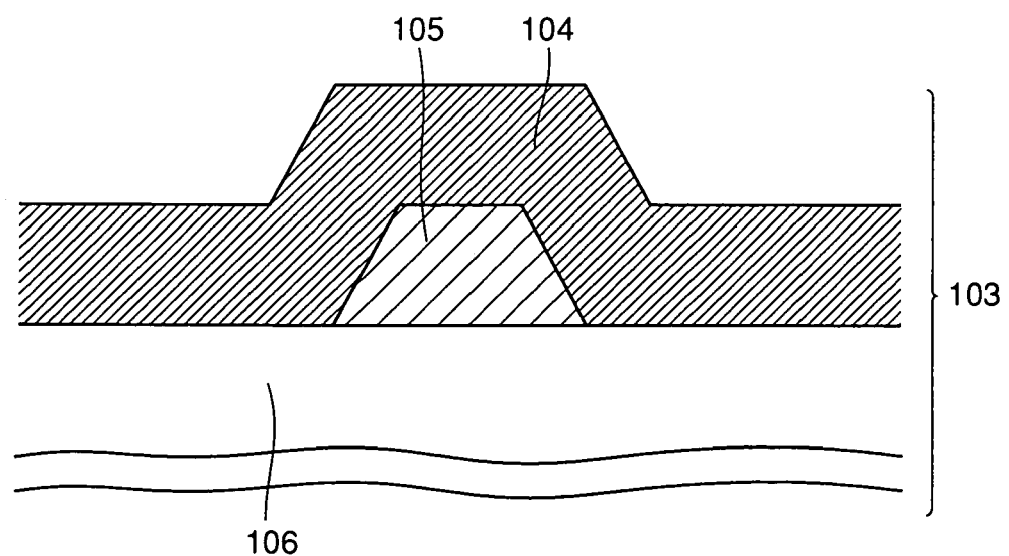
FIG. 2 shows an example of a substrate that cannot have the film thickness measured.
Figure 3:
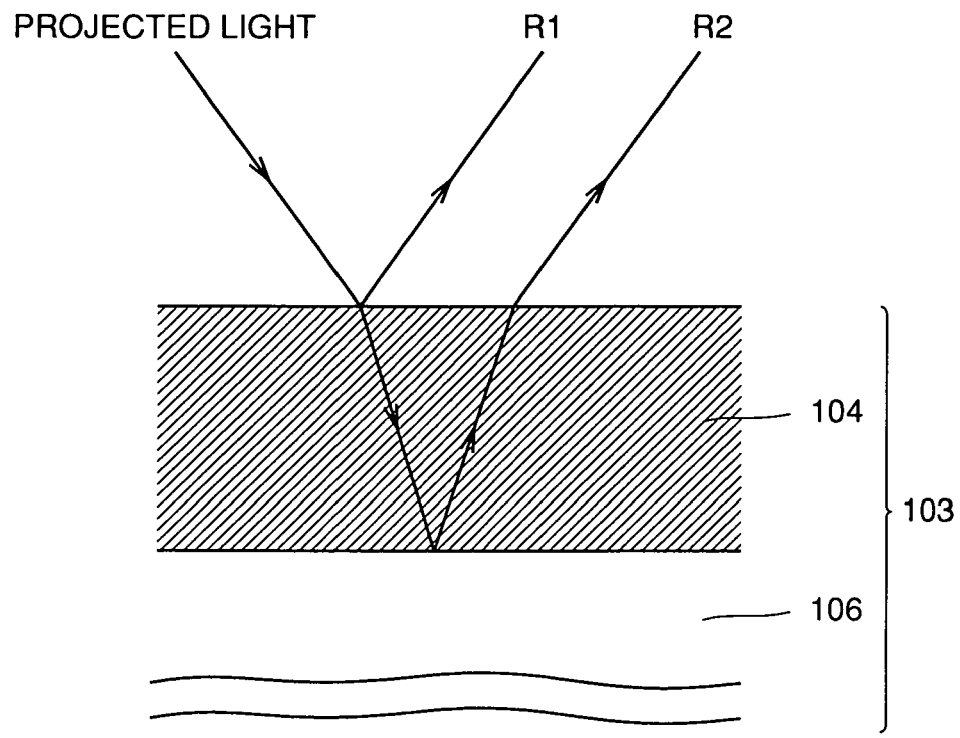
FIG. 3 is a diagram to describe an example of the conventional light interference method.
Figure 4:
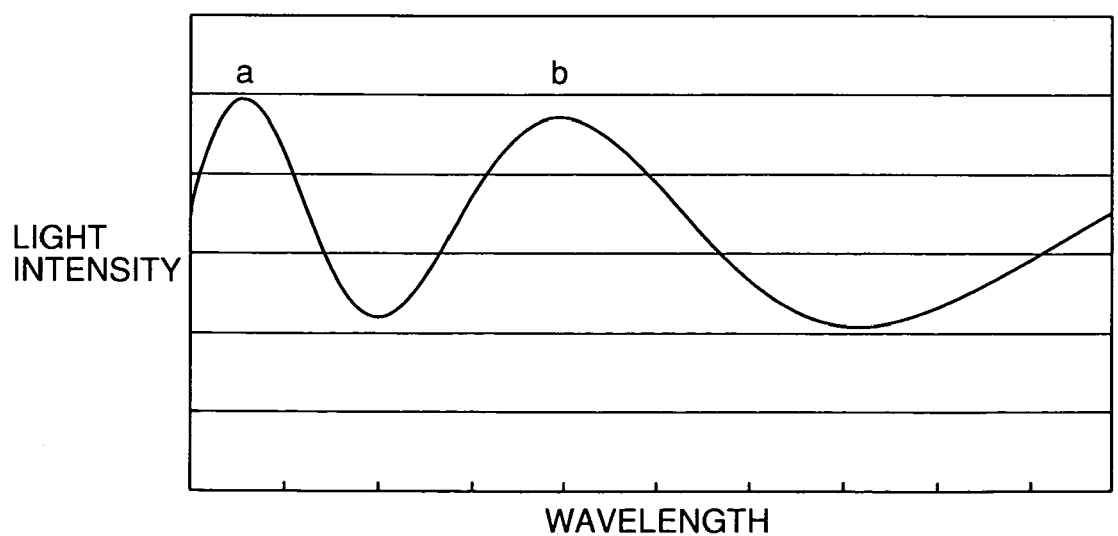
FIG. 4 shows an example of the relationship between reflected light wavelength and light intensity.
Figure 5:
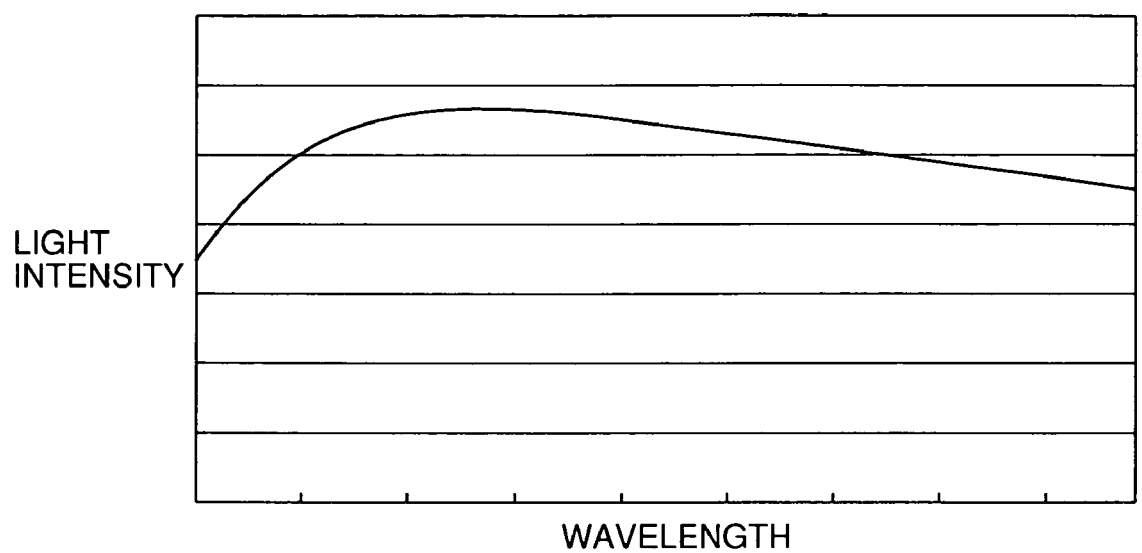
FIG. 5 shows an example of a wavelength-light intensity curve when the film thickness cannot be measured by the peak valley method.
Figure 6:
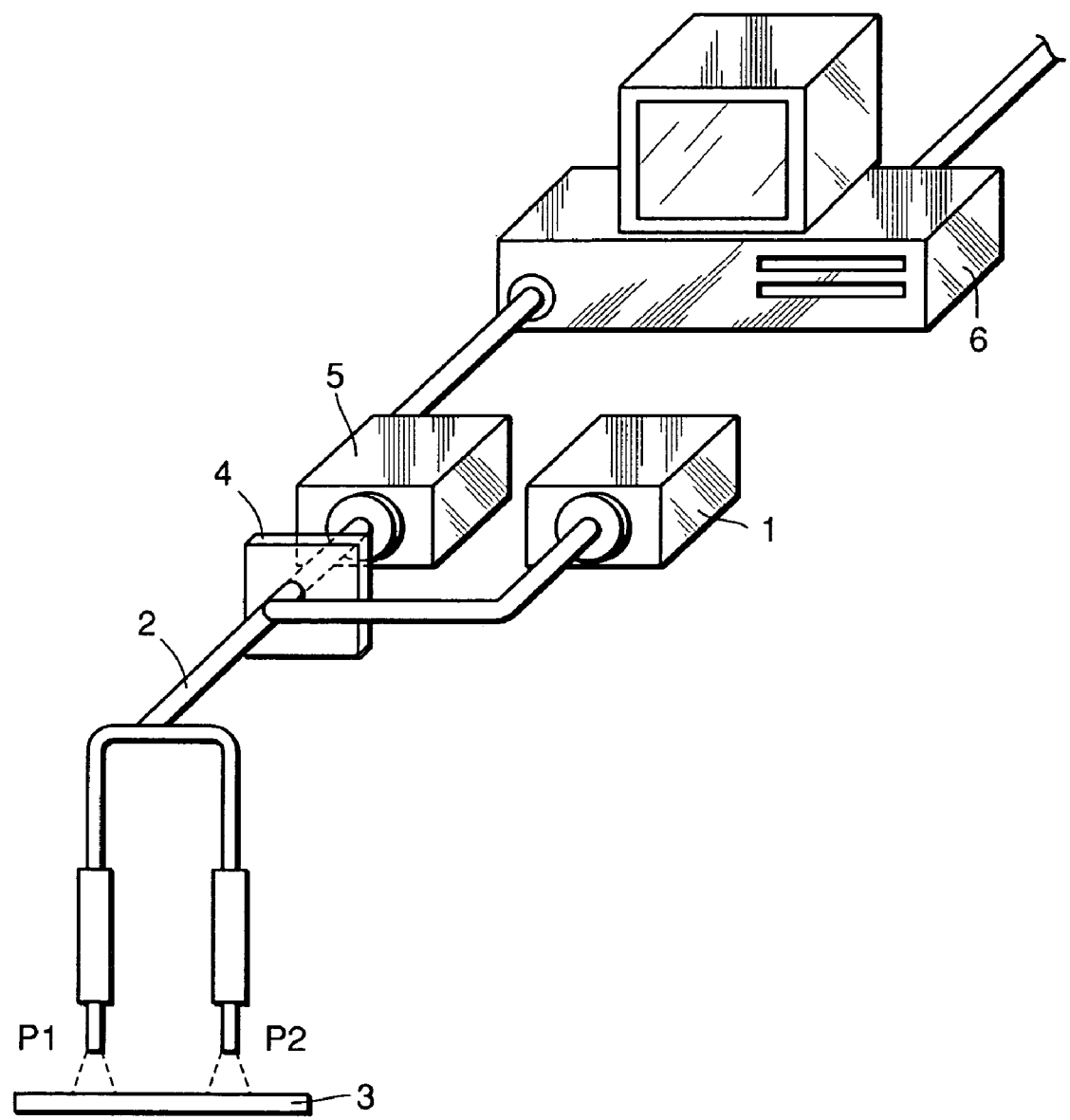
FIG. 6 is a block diagram to describe a structure of a thin film thickness measurement apparatus according to a first embodiment of the present invention.

Referring to FIG. 6, a thin film thickness measurement apparatus according to the first embodiment of the present invention includes a light source 1, a branch type optical fiber 2 guiding light from light source 1 onto a substrate 3, and receiving light reflected from substrate 3, a light restriction shutter 4 selectively blocking the plurality of reflected light from substrate 3, a spectroscope 5 dividing the reflected light guided by branch type optical fiber 2 according to light intensity of each wavelength, and a computer 6 analyzing light intensity of each wavelength to analyze the thickness of the thin film.

In order to allow thickness measurement of any thin film, a halogen lamp or the like that can emit light having a constant wavelength range (for example, a wavelength range of approximately 400–800 nm in visible light region) for light source 1. As to the optical components of spectroscope 5 and the like, components that can cover that wavelength range are used.

Figure 7:
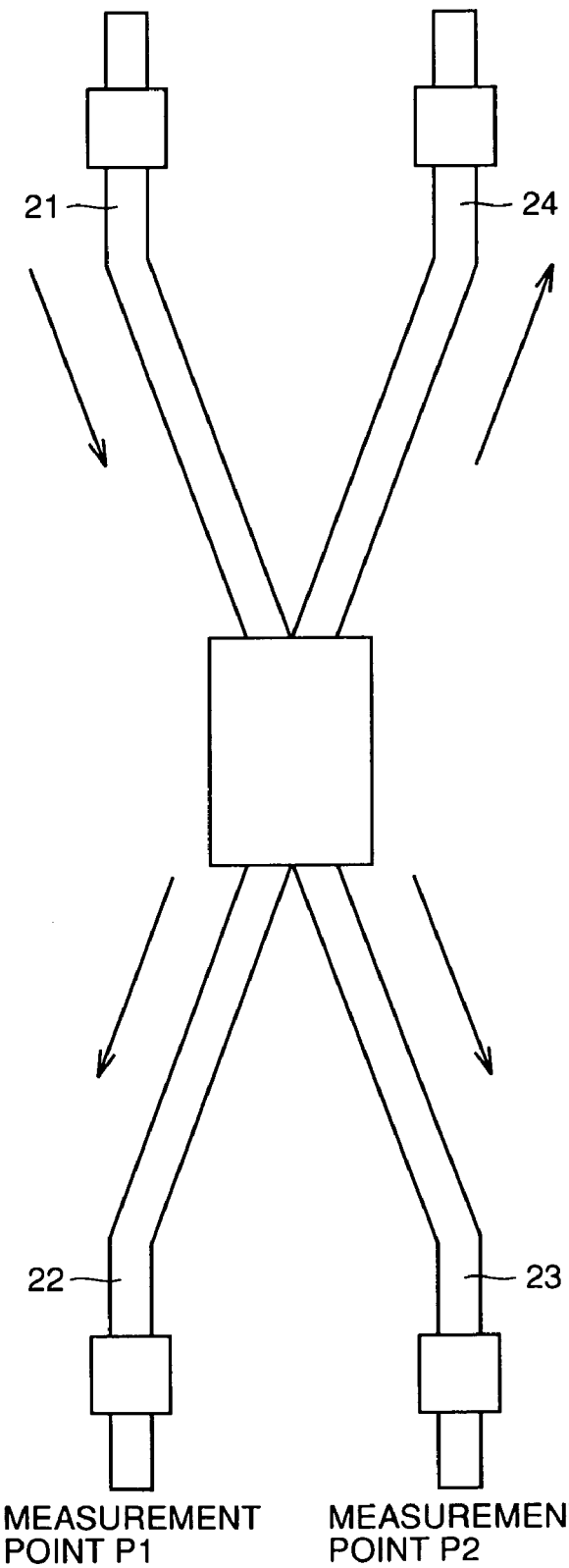
FIG. 7 is a diagram to describe a structure of a branch type optical fiber 2.

Referring to FIG. 7, branch type optical fiber 2 includes an optical fiber 21 guiding the light from light source 1 on substrate 3, an optical fiber 22 guiding the light from light source 1 to a measurement point P1 on substrate 3 and guiding light reflected from measurement point P1 on substrate 3 to spectroscope 5, an optical fiber 23 guiding light from light source 1 to a measurement point P2 on substrate 3 and guiding light reflected from measurement point P2 on substrate 3 to spectroscope 5, and an optical fiber 24 guiding reflected light from measurement point P1 and reflected light from measurement point P2 on substrate 3 to spectroscope 5.

Figure 8:
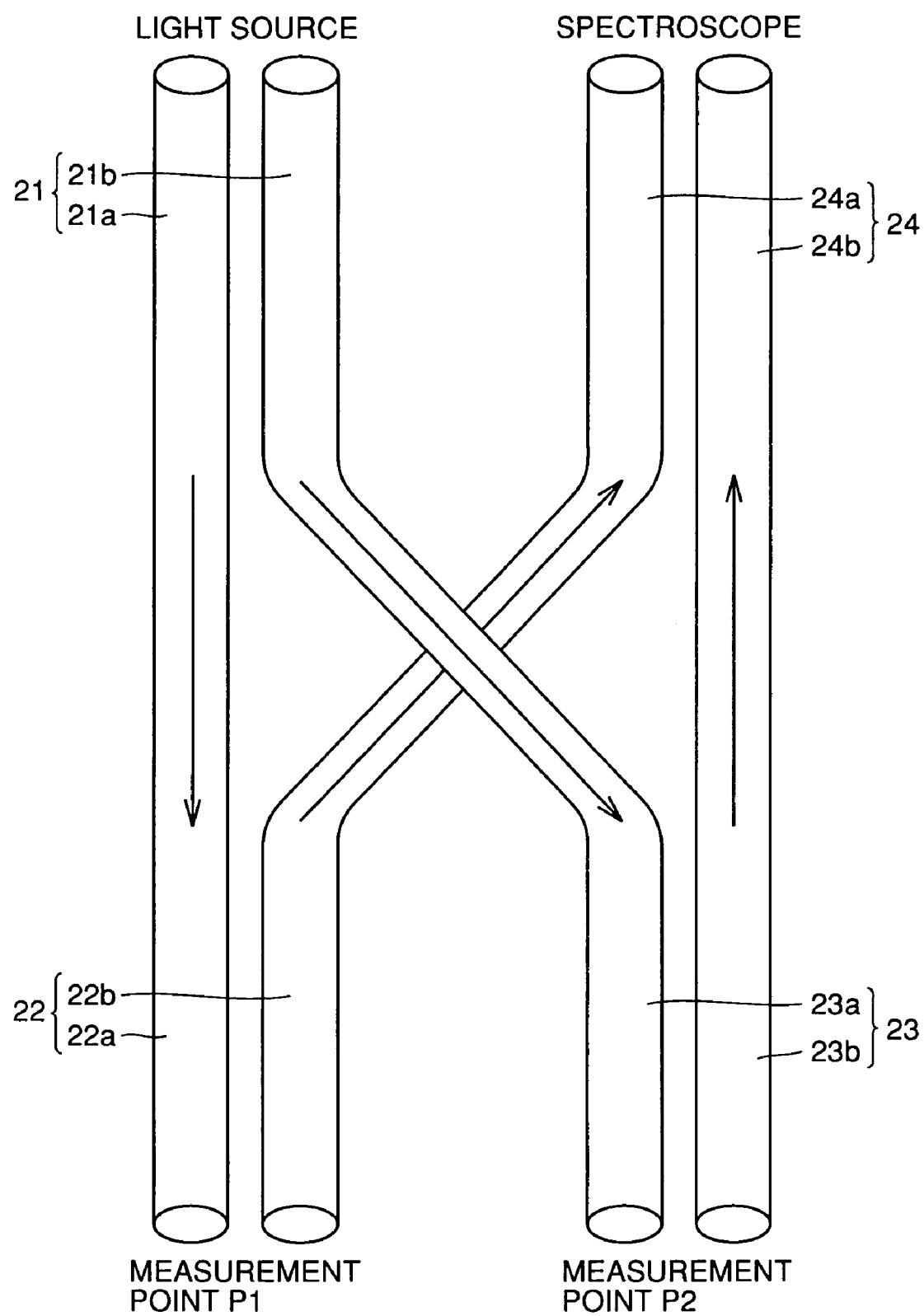
FIG. 8 is a diagram to describe in further detail branch type optical fiber 2.

Referring to FIG. 8, optical fiber 21 of FIG. 7 includes two optical fibers 21a and 21b. Optical fiber 21a directs the light from light source 1 to measurement point P1 on substrate 3. Optical fiber 21b directs light from light source 1 to measurement point P2 on substrate 3.

Optical fiber 22 of FIG. 7 includes two optical fibers 22a and 22b. Optical fiber 22a directs light from light source 1 to measurement point P1 on substrate 3 and forms one optical fiber with optical fiber 21a. Optical fiber 22b directs light reflected from measurement point P1 on substrate 3 to spectroscope 5.

Optical fiber 23 of FIG. 7 includes two optical fibers 23a and 23b. Optical fiber 23a directs light from light source 1 to measurement point P2 on substrate 3, and forms one optical fiber with optical fiber 21b. Optical fiber 23b directs light reflected from measurement point P2 on substrate 3 to spectroscope 5.

Optical fiber 24 of the FIG. 7 includes two optical fibers 24a and 24b. Optical fiber 24a directs reflected light from measurement point P1 on substrate 3 to spectroscope 5, and forms one optical fiber with optical fiber 22b. Optical fiber 24b directs reflected light from measurement point P2 on substrate 3 to spectroscope 5, and forms one optical fiber with optical fiber 23b.

Figure 9:
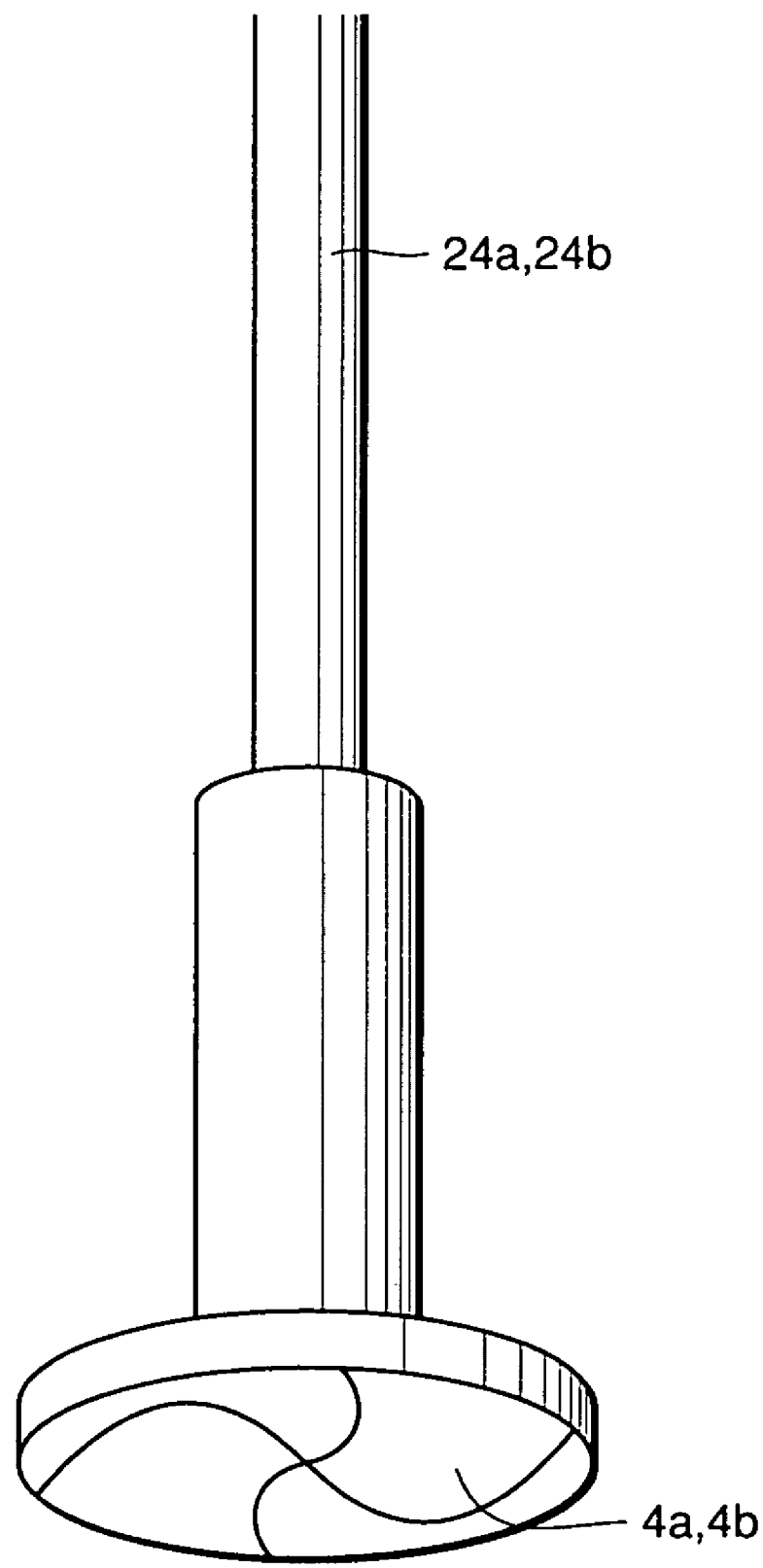
FIG. 9 is a diagram to describe a structure of a light restriction shutter.

Referring to FIG. 9, light restriction shutter 4 of FIG. 6 is provided at the leading edge of optical fibers 24a and 24b shown in FIG. 8 (between optical fibers 24a, 24b and spectroscope 5). Light restriction shutter 4a provided at the leading edge of optical fiber 24a open/closes to control the passage and blocking of reflected light from measurement point P1 on substrate 3. Light restriction shutter 4b provided at the leading end of optical fiber 24b open/closes to control the passage and blocking of reflected light from measurement point P2 on substrate 3. Only one of the reflected light from measurement point P1 and measurement point P2 on substrate 3 can be selected and guided to spectroscope 5 by opening one and closing the other of the light restriction shutters. Furthermore, the average value of the film thickness at measurement points P1 and P2 on substrate 3 can be measured by simultaneously opening light restriction shutters 4a and 4b.

Figure 10:
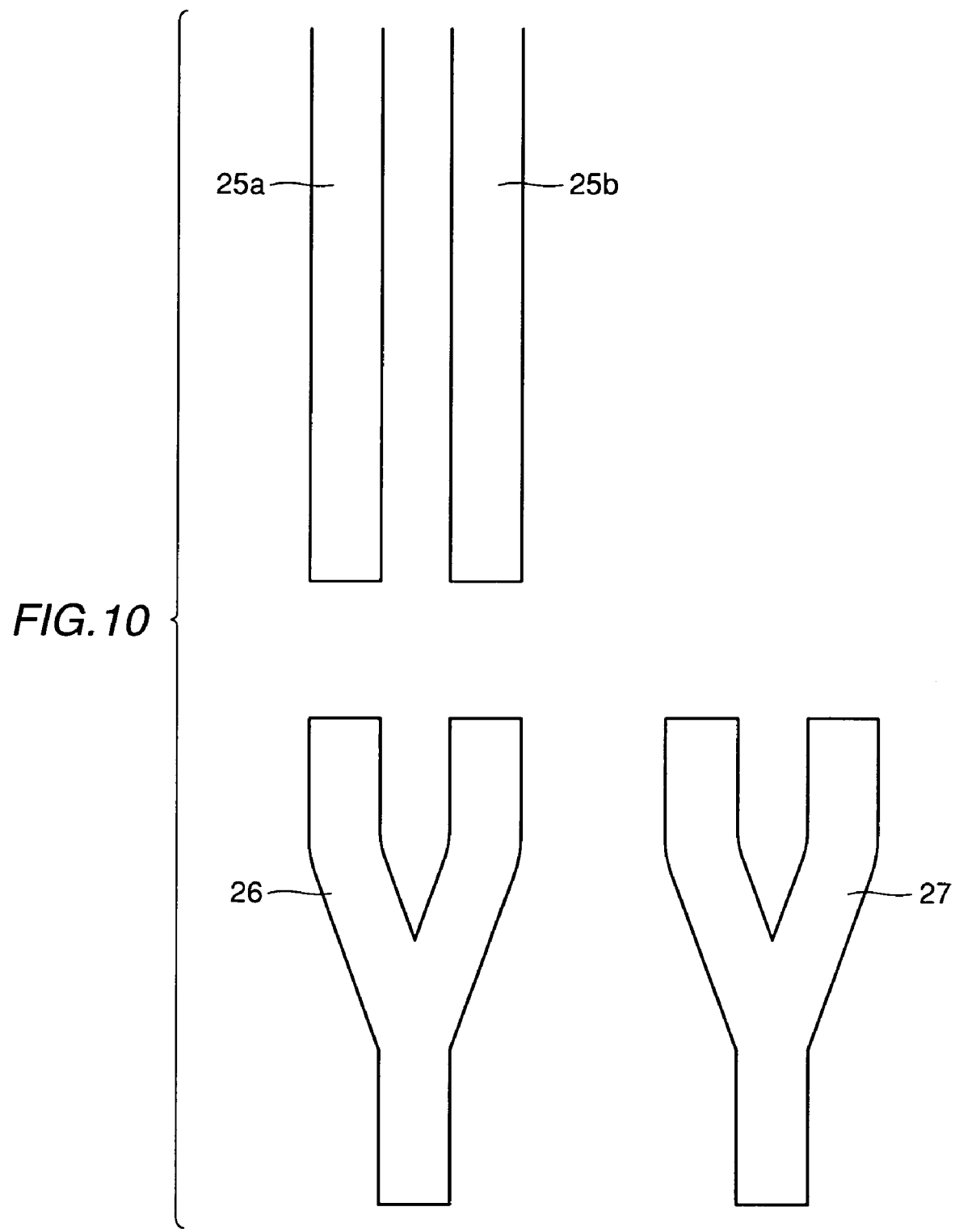
FIG. 10 shows an another example of an optical fiber to measure a plurality of points.

Another example of the branch type optical fiber will be described with reference to FIG. 10. When there is always only one point of measurement on substrate 3, optical fiber 25a guiding light from light source 1 and optical fiber 25b guiding reflected light to spectroscope 5 as shown in FIG. 10 can be connected to optical fiber 26 provided at measurement point P1 or optical fiber 27 provided at measurement point P2 on substrate 3. The thickness of either measurement point P1 or P2 can be measured.

Figure 11:
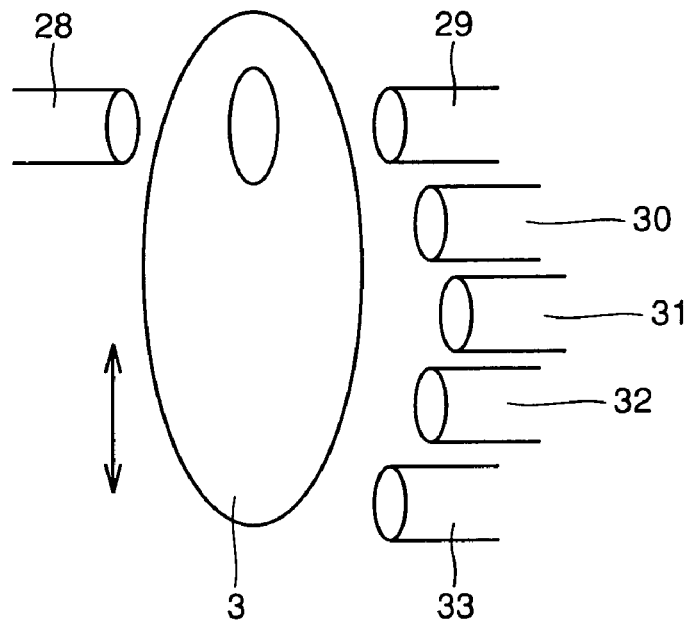
FIG. 11 is another example of an optical fiber to measure a plurality of points.

Alternatively, an optical fiber 28 guiding light from light source 1 can be provided in a movable manner, and a plurality of optical fibers 29–33 receiving reflected light from substrate 3 can be provided, as shown in FIG. 11. A plurality of points on substrate 3 can be measured by moving only optical fiber 28.

Figure 12:
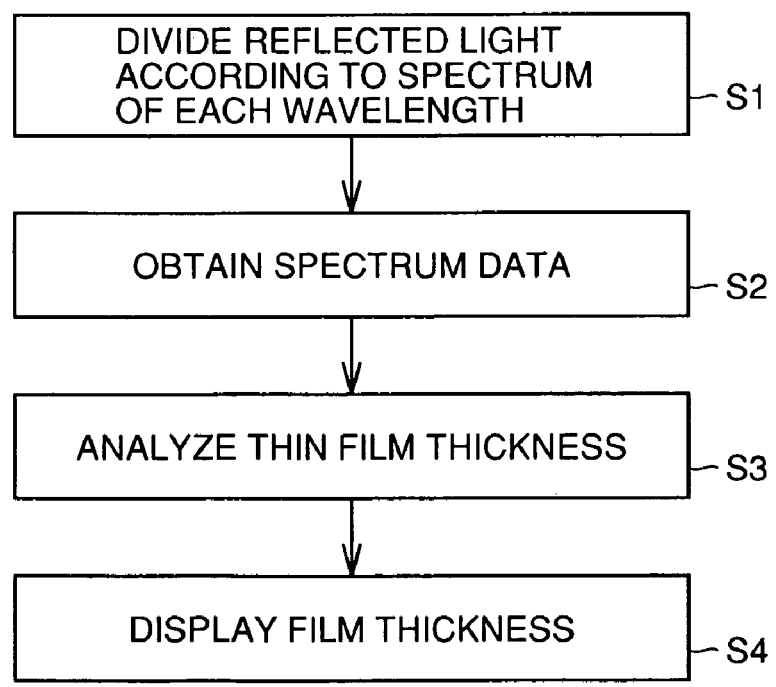
FIG. 12 is a flow chart of the procedure of the thin film thickness measurement apparatus according to the first embodiment.

The procedure of the film thickness measurement process executed by computer 6 will be described with reference to FIG. 12. Reflected light from substrate 3 is divided into the light intensity (spectrum) for each wavelength by spectroscope 5 (S1). Computer 6 receives the spectrum data for each wavelength from spectroscope 5 (S2), analyzes the thickness of the thin film using a logic expression (S3), and displays the obtained film thickness on a screen of computer 6 (S4).

The logic expression to analyze the thickness of the thin film will be described here. The light intensity R of reflected light from the substrate can be represented by equations (2)–(7), where $n_0$ is the refractive index of the substrate, $n_1$ is the refractive index of the thin film, $n_2$ is the refractive index of air, k is the absorption coefficient of the thin film, d is the thickness of the thin film, and $\lambda$ is the wavelength of the light source.

Optical constants (n, k) are numerics that change depending on the light wavelength $\lambda$ from the light source. The film thickness d of the thin film can be calculated by altering the optical constants (n, k) corresponding to wavelength $\lambda$ of light and inserting the same into equation (2). More specifically, thin film thickness d can be calculated when optical constants (n, k) are known, and if there is a wavelength-light intensity curve produced using light intensity of each wavelength detected by spectroscope 5.

When optical constants (n, k) are not known, optical constants (n, k) and thin film thickness k can be obtained as set forth in the following.

(1) Rough numerics are inserted into equation (2) as the initial values for film thickness d, refractive index $n_1$ and absorption coefficient k of the target thin film.

(2) The upper limit value and lower limit value of respective parameters d, $n_1$ and k are set. For example, the upper and lower limit values of thin film thickness d is set to ±50% the initial value.

(3) Parameters d, $n_1$ and k are inserted into equation (2) altered within the range between the upper limit value and the lower limit value. The value of each parameter is calculated so that the resultant curve is closest to the curve of the actually measured wavelength-light intensity. As a determination method thereof, the difference of light intensity between both curves is obtained for each wavelength. The parameters are altered so that the total sum of the differences at the measured wavelength range is smallest. Thus, respective parameters can be obtained. Optical constants (n, k) and thin film thickness d can be obtained at the same time by this method.

In the case where a multi layered structure of the thin film is formed on the substrate, the film thickness of each thin film can be calculated according to a method similar to that above, provided that the logic expression of light intensity R(p+1,0) of light reflected from the substrate is represented by equations (19)–(22) and (12)–(18), where n(0) is the refractive index of the substrate, n(p) is the refractive index of the p-th layer of thin film from the substrate, n(p+1) is the refractive index of air, k is the absorption coefficient of the p-th layer of thin film from the substrate, d(p) is the thin film thickness, and λ is the wavelength of the light source.

$$R(p+1, 0) = \frac{A+B}{1+C+B} \quad (19)$$

$$A = R(p+1,p) + R(p,0) \times k^2 \quad (20)$$

$$B = 2 \times \rho(p+1,p) \times \sqrt{R(p,0)} \times k \times \cos(\gamma(p,0) + \gamma(p)) \quad (21)$$

$$C = R(p+1,p) \times R(p,0) \times k^2 \quad (22)$$

By inserting values sequentially into the logic expression from the first layer of thin film, the second layer of thin film, . . . from the substrate, i.e., by sequentially inserting 1, 2, . . . into p, the optical constants and thickness of respective thin films can be obtained whatever layer the thin film may be located. It is to be noted that the time required for computation increases since there are more parameters in proportion to more layers of the thin film. Also, it is to be noted that the error becomes greater as a function of the number of thin films from the stand point of measurement accuracy.

Computer 6 can notify generation of a defect to the film growth apparatus through communication or develop a database that is to be referred to in setting the film growth conditions for the film growth apparatus, according to the obtained thin film thickness d.

An example of installing the thin film thickness measurement apparatus of the present invention will be described with the reference to FIGS. 13A and 13B. Sensor 10 in which branch type optical fiber 2 of FIG. 6 is provided is located above a gate opening (gate valve) 13 of a film growth apparatus so that sensor 10 is substantially perpendicular to substrate 3 where a thin film is formed. This film growth apparatus carries out film growth by, for example, CVD (Chemical Vapor Deposition), and places a plurality of substrates with grown films on respective trays. The plurality of substrates are stored in a load rock 14 provided in a gate opening 13 of the unload chamber shown in FIG. 13B. A substrate transportation robot 11 takes out one substrate from load rock 14 and places the same on a robot hand 12, and moves so that substrate 3 is located right under sensor 10. In the case where there are a plurality of measurement points of the thin film, robot 11 moves every time measurement of a measurement point ends so that the next point of measurement is located right below sensor 10. FIG. 13C shows the configuration of robot hand 12.

Figure 14A:
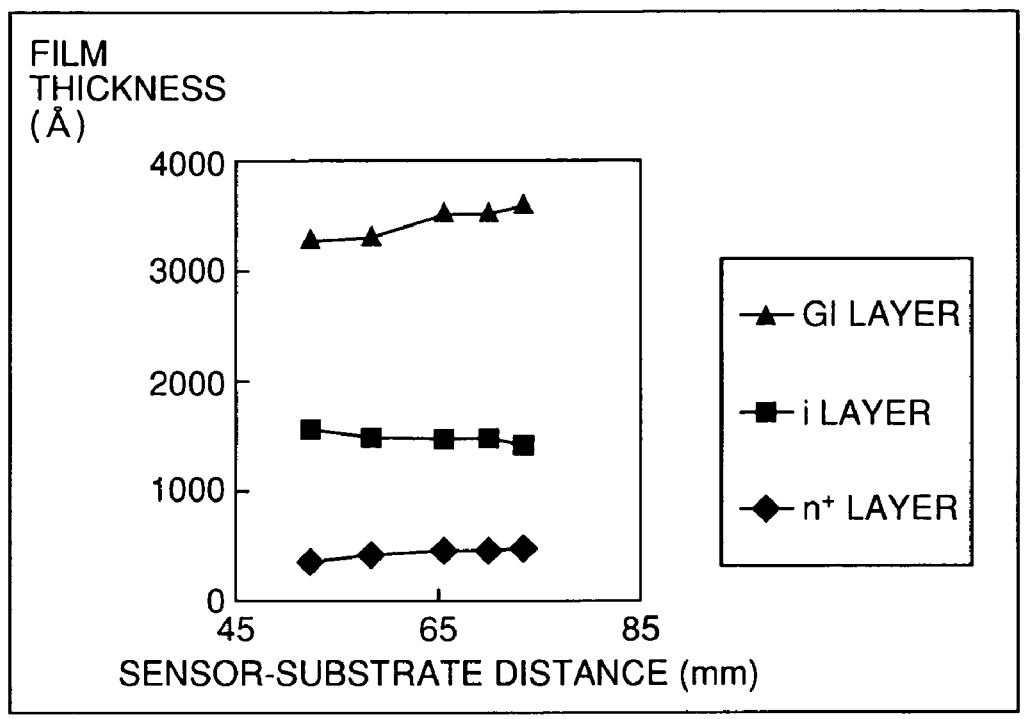
FIG. 14A is a diagram to describe the effect of vertical deviation of the substrate on the measured value.

The effect of vertical deviation and inclination of the substrate on the measured value will be described with reference to FIGS. 14A and 14B. In FIG. 14A, the distance between sensor 10 and substrate 3 is plotted along the abscissa, and the thickness of the thin film measured by the thin film thickness measurement apparatus of the present embodiment is plotted along the ordinate. It is appreciated from FIG. 14A that the measured result is hardly affected by the distance between sensor 10 and substrate 3 in any of the GI layer (silicon nitride), i layer (amorphous silicon) and $n^+$ layer ($n^+$ type amorphous silicon).

Figure 14B:
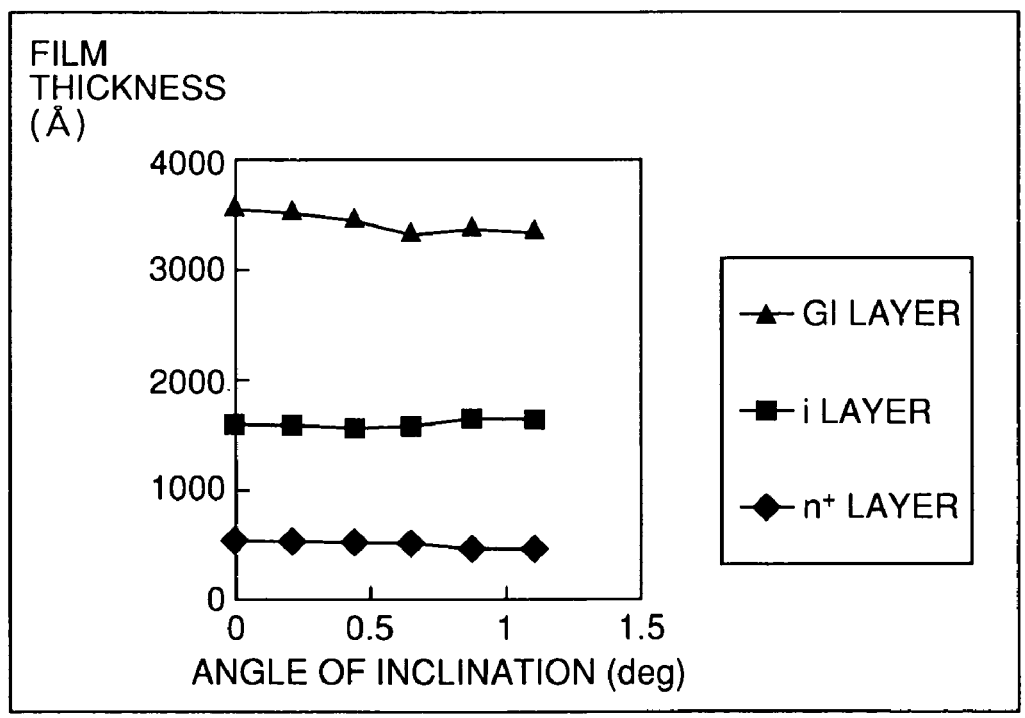
FIG. 14B is a diagram to describe the effect of inclination of the substrate on the measured value.

In FIG. 14B, the angle of inclination of substrate 3 is plotted along the abscissa, and the thickness of the thin film measured by the thin film thickness measurement apparatus of the present embodiment is plotted along the ordinate. It is appreciated from FIG. 14B that the measurement result is hardly affected by the inclination angle of substrate 3 in any of the GI layer, i layer and $n^+$ layer.

According to the thin film thickness measurement apparatus of the present embodiment, the thickness of the thin film of the substrate can be measured immediately after the film growth step. Therefore, a defective substrate, if any, can be detected immediately after film growth. There is hardly no delay of finding a defective substrate from the film growth of the substrate. Any damage caused by generation of a defective product can be suppressed to the minimum.

By generating a database from the film growth conditions and thin film thickness, the film growth status such as the tendency of the film of the substrate can be predicted.

The structure of sensor portion of the film thickness measurement apparatus is extremely simple, and reduction in size and weight is allowed. Therefore, the restriction in installing an existing film growth apparatus can be alleviated, and maintenance thereof facilitated.

The thickness measurement apparatus can analyze the thickness of the thin film exclusively by a wavelength-light intensity curve. It is therefore possible to measure the thickness of the thin film in a short period of time (approximately one second per measurement point). Film thickness error is suppressed since analysis is carried out taking into consideration the absorption coefficient of the thin film.

Furthermore, measurement of a plurality of points on the substrate is allowed in a short period of time by the usage of a branch type optical fiber and arrangement of a plurality of optical fibers.

Second Embodiment

Figure 15:
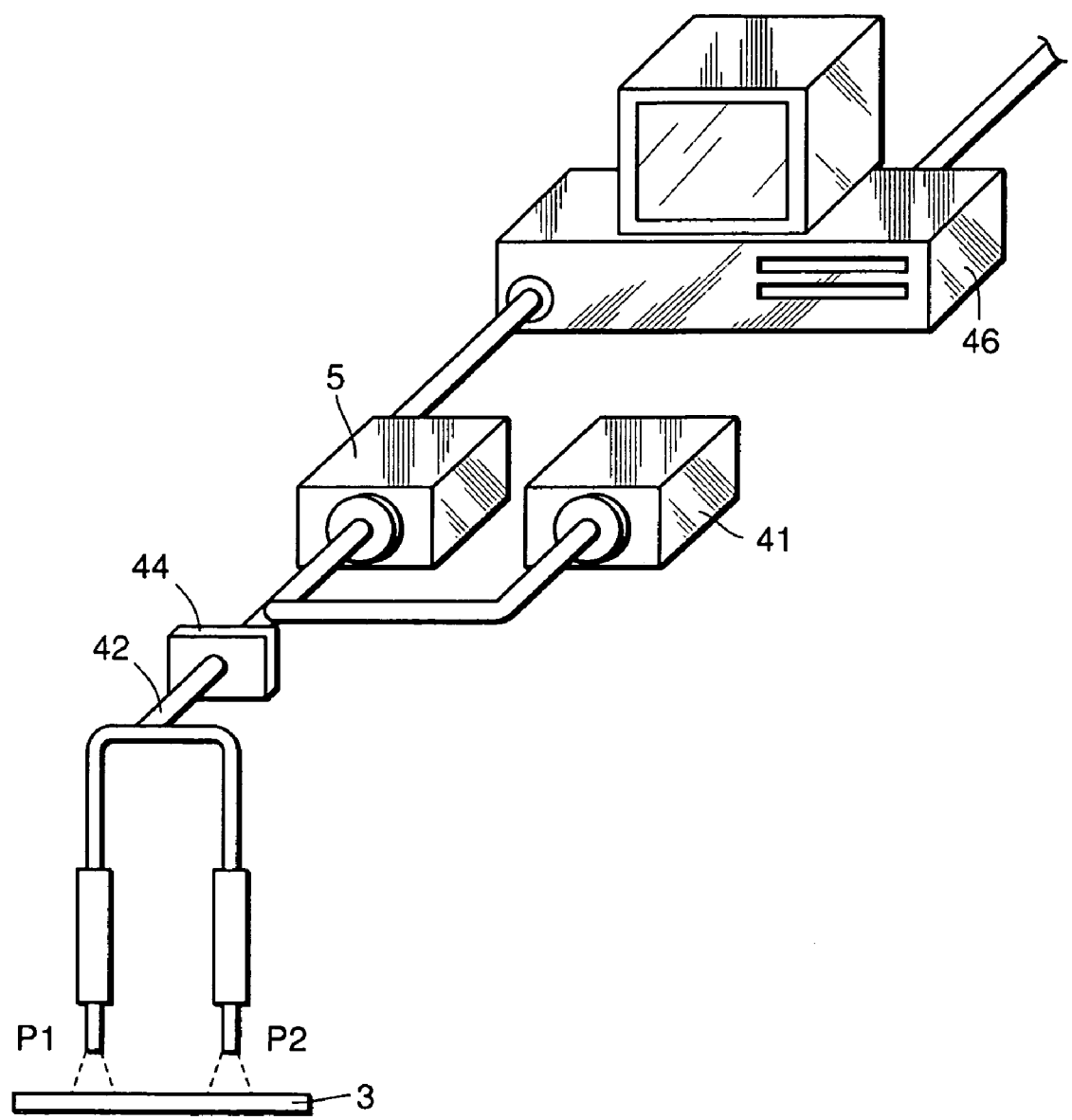
FIG. 15 is a diagram to describe a structure of a thin film thickness measurement apparatus according to a second embodiment of the present invention.

Referring to FIG. 15, a thin film thickness measurement apparatus of the second embodiment includes a light source 41, a branch type optical fiber 42 guiding light from light source 41 to a plurality of sites (here, two) on substrate 3, and receiving light reflected from respective sites of substrate 3, a light restriction shutter 44 selectively blocking incident light to be guided to a plurality of sites of substrate 3 and a plurality of reflected light from substrate 3, a spectroscope 5 dividing reflected light guided by branch type optical fiber 42 according to light intensity for each wavelength, and a computer 46 analyzing the light intensity by each wavelength to calculate the thickness of the thin film.

Components similar to those of the thin film thickness measurement apparatus of the first embodiment have the same reference character allotted, and detailed description thereof will not be repeated.

A halogen lamp that has a wavelength range (400–850 nm) approximating a visible light wavelength range (400–800 nm), for example, is employed as light source 41. However, another lamp can be provided in the same chamber or in another chamber of the light source of the halogen lamp. The lamps are used lit at the same time or lit in a switching manner. Optical components of spectroscope 5 and the like are used that can cover the wavelength range thereof.

Figure 16:
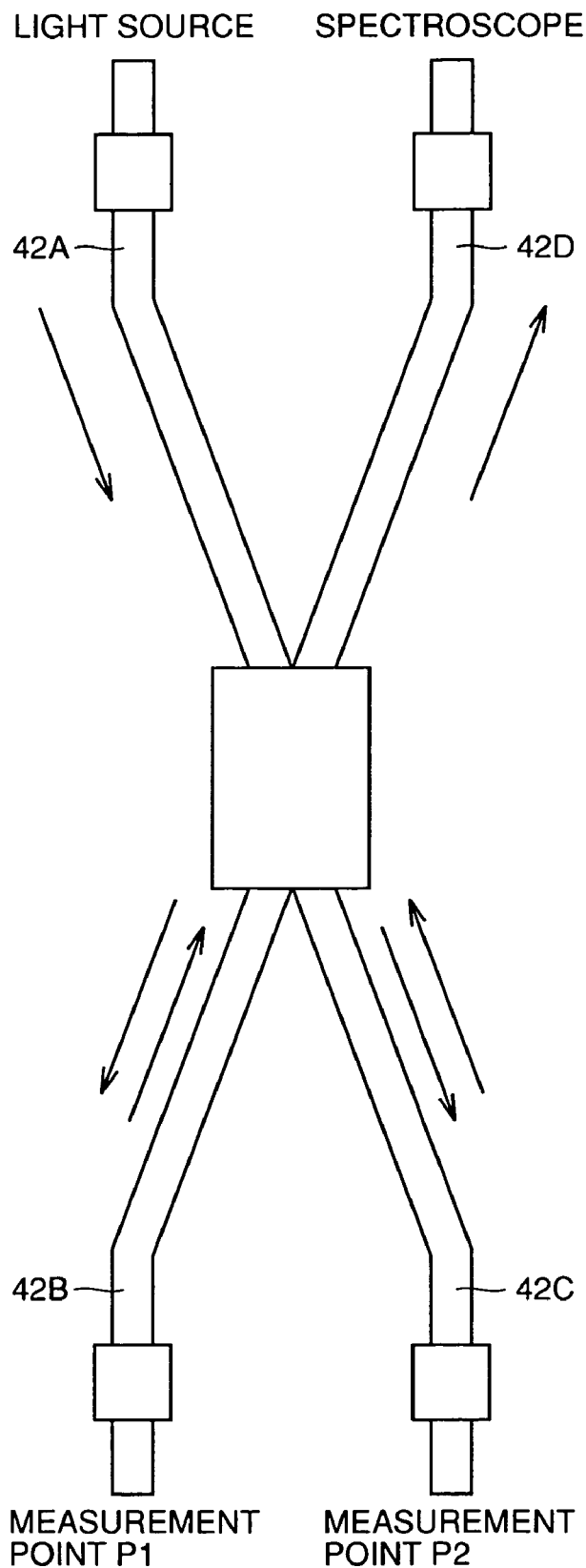
FIG. 16 is a diagram to describe a structure of a branch type optical fiber 42.

Referring to FIG. 16, branch type optical fiber 42 includes an optical fiber 42A guiding light from light source 41 to substrate 3, an optical fiber 42B guiding light from light source 41 onto a measurement point P1 on substrate 3 and guiding light reflected from measurement point P1 on substrate 3 to spectroscope 5, an optical fiber 42C guiding the light from light source 1 to a measurement point P2 on substrate 3, and guiding light reflected from measurement point P2 on substrate 3 to spectroscope 5, and an optical fiber 42D guiding reflected light from measurement point P1 and reflected light from measurement point P2 on substrate 3 to spectroscope 5.

Branch type optical fiber 2 will be described in further detail with reference to FIG. 17. Optical fiber 42A includes two groups of optical fibers 42AA and 42AB. Optical fiber 42AA directs light from light source 41 onto measurement point P1 on substrate 3. Optical fiber 42AB directs light from light source 41 onto measurement point P2 on substrate 3.

Optical fiber 42B includes two groups of optical fibers 42BA and 42BB. Optical fiber 42BA directs light from light source 41 to measurement point P1 on substrate 3. Optical fiber 42BB directs reflected light from measurement point P1 on substrate 3 to spectroscope 5.

Optical fiber 42C includes two groups of optical fibers 42CA and 42CB. Optical fiber 42CA directs light from light source 41 to measurement point P2 on substrate 3. Optical fiber 42CB directs reflected light from measurement point P2 on substrate 3 to spectroscope 5.

Optical fiber 42D includes two groups of optical fibers 42DA and 42DB. Optical fiber 42DA directs reflected light from measurement point P1 on substrate 3 to spectroscope 5. Optical fiber 42DB directs reflected light from measurement point P2 on substrate 3 to spectroscope 5.

Figure 17:
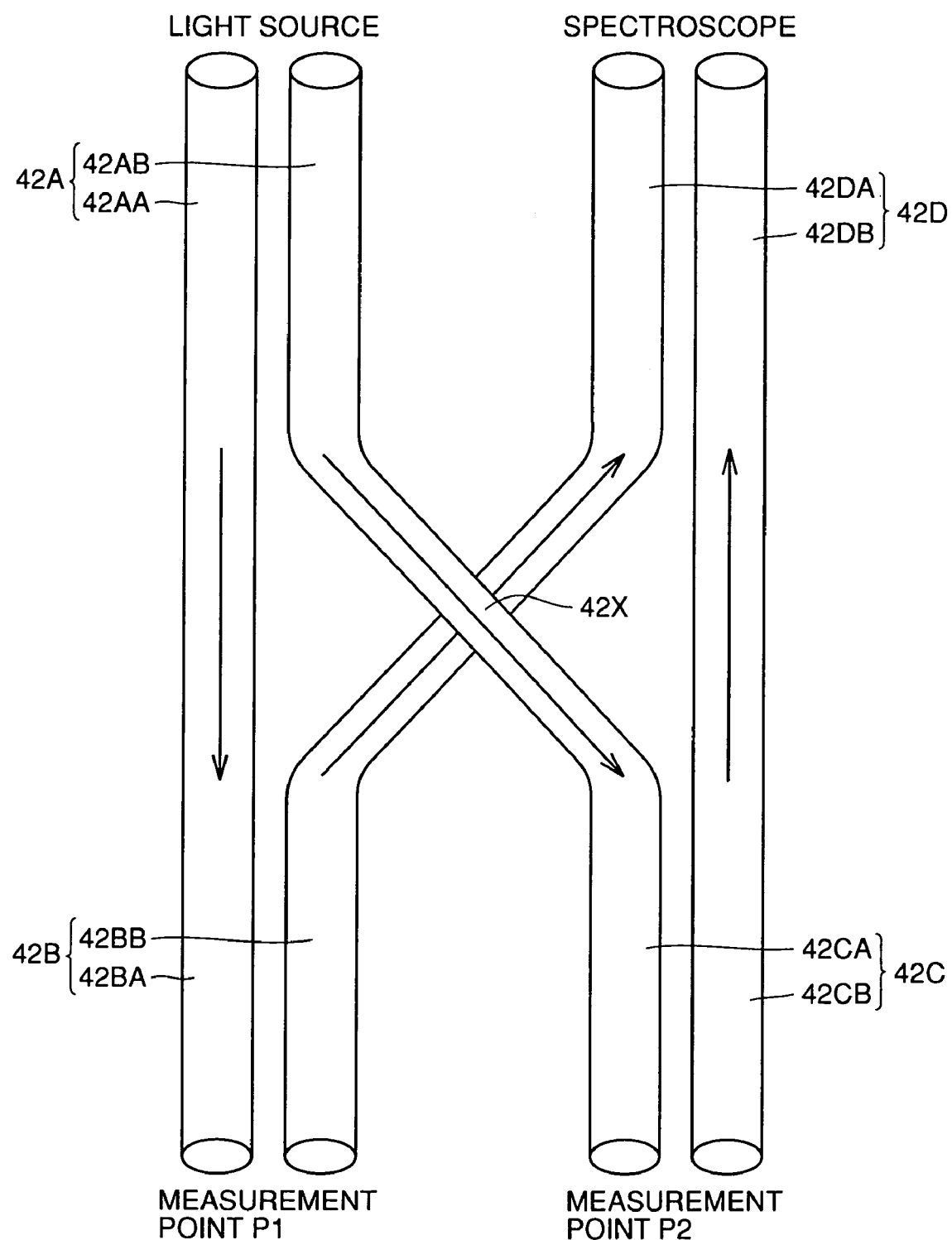
FIG. 17 is a diagram to describe in further detail branch type optical fiber 42.
Figure 18:
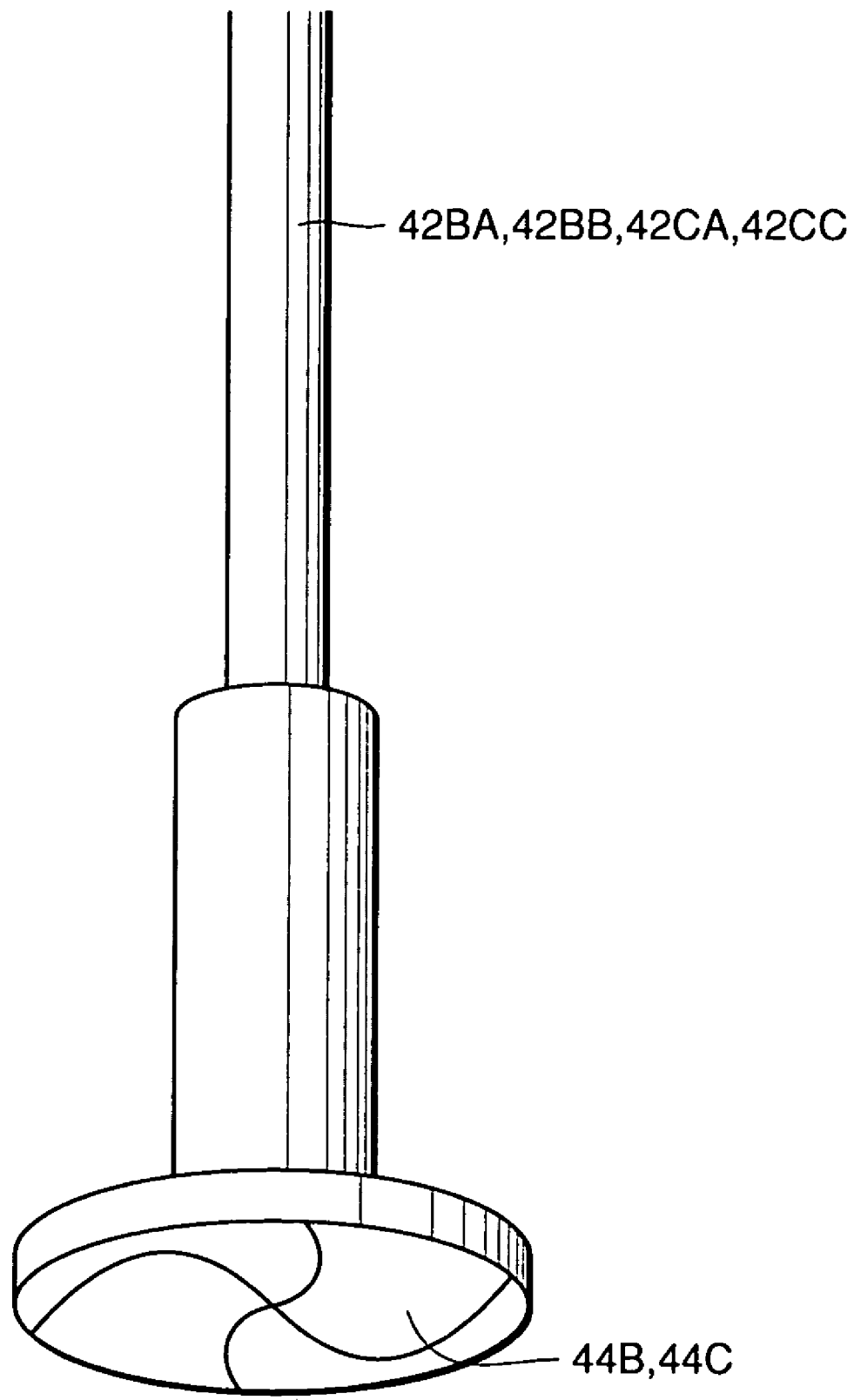
FIG. 18 is a diagram to describe a structure of a light restriction shutter.

Referring to FIG. 18, light restriction shutter 44 is provided in the path of optical fibers 42B and 42C showing FIG. 17. More specifically, light restriction shutter 44 is provided between the connection point 42X between optical fibers 42A and 42C (connection point between optical fibers 42D and 42B) and measurement points P1 and P2. Light restriction shutter 44B provided in the path of optical fiber 42B is opened/closed to control the switching of passage and blocking of incident light to measurement point P1 on substrate 3 and reflected light from measurement point P1. Light restriction shutter 44C provided in the path of optical fiber 42C is opened/closed to control the switching of passage and blocking of incident light to measurement point P2 and reflected light from measurement point P2 on substrate 3. By closing one and opening the other of light restriction shutters 44B and 44C, one of the reflected light from measurement point P1 or P2 on substrate 3 can be selectively guided to spectroscope 5. Also, by opening light restriction shutters 44B and 44C simultaneously, the average value of the film thickness at measurement points P1 and P2 on substrate 3 can be obtained.

Figure 19:
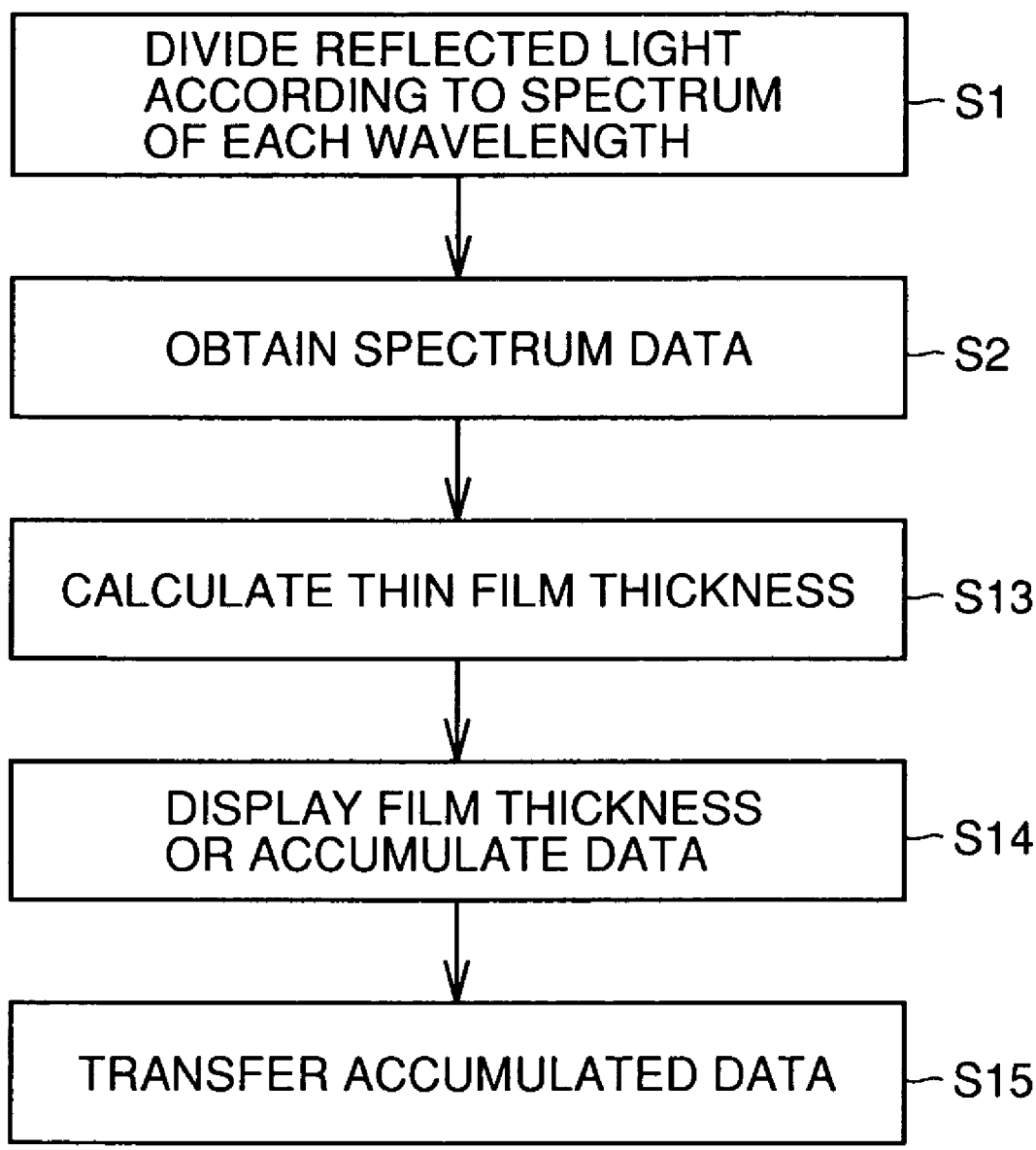
FIG. 19 is a flow chart of the procedure of the thin film thickness measurement apparatus of the second embodiment.

The procedure of the film thickness measurement process executed by computer 46 will be described with reference to FIG. 19. The reflected light from substrate 3 is divided into light intensity (spectrum) of each wavelength by spectroscope 5 (S1). Computer 46 receives spectrum data for each wavelength from spectroscope 5 (S2), and calculates the thickness of the thin film using a logic expression that will be described afterwards (S13). Computer 46 displays the obtained film thickness on a screen of computer 46, and stores the data in an accumulated manner (S14). Computer 46 transfers the accumulated data to a centralized controller (not shown) (S15).

The centralized controller receiving data related to the thickness of the thin film from computer 46 carries out a process corresponding to occurrence of an abnormal status such as effecting an alarm when the thin film thickness exceeds a predetermined reference value, when the difference in film thickness between measurement points in the substrate is great, or when change in the film thickness of a certain measurement point is great over time.

An example of the thin film thickness analyze method will be described here. When the thin film formed on substrate 3 is of a single layer, reflected light intensity R from substrate 3 can be represented by equations (2)–(7), similar to the first embodiment. Therefore, details thereof will not be repeated here.

The thickness of a thin film of each layer can be calculated by a similar manner even in the case where a multi layered thin film is formed on the substrate. The relationship represented by equations (8)–(18) is established between reflected light intensity $R(p+1,0)$ from the substrate and respective parameters, where $n(0)$ is the refractive index of substrate, $n(p)$ is the refractive index of the p-th layer of thin film from the substrate, $n(p+1)$ is the refractive index of air, $k(p)$ is the absorption coefficient of the p-th layer of thin film from the substrate, $d(p)$ is the thin film thickness of the p-th layer from the substrate, and $\lambda$ is the wavelength of the light source.

By inserting values sequentially into the logic expression for the first layer of thin film, the second layer of thin film, . . . from the substrate. i.e. by sequentially inserting 1, 2, . . . for p, the optical constants ($n(p)$, $k(p)$) and thickness $d(p)$ of respective films can be obtained irrespective of how many layers the thin film may be formed of. When thin films having optical constants that are close to each other are stacked adjacent to each other, analysis is carried out with those thin films as the same one layer. The time required for computation increases since there are more number of parameters as the number of thin films increases. Also, the error from the actual value increases as there are more thin films. However, it has been confirmed by the inventors of the present inventors that measurement in-line is allowed even for approximately three layers in a liquid crystal display.

The number of measurement sites on the substrate may be one in order to identify error in the liquid crystal display. However, there is a possibility of local abnormal film thickness in the substrate for liquid crystal displays of a size at least 1 M square in which the thickness of thin films differ partially. It is therefore desirable to measure approximately 3–5 points on one substrate.

An example of installing the thin film thickness measurement apparatus of the present embodiment will be described with reference to FIGS. 20A and 20B. As shown in FIG. 20A, a sensor unit 50 in which branch type optical fiber 42 of the FIG. 15 is provided is fixed to a support 50A provided in the film growth apparatus. Branch type optical fiber 42 is arranged all over in support 50A. Sensor unit 50 is attached to direct light substantially perpendicular to substrate 3 located in the proximity of a gate opening (referred to as "gate valve" hereinafter) of the growth apparatus. The distance of at least 10 mm is required between substrate 3 and sensor unit 50 so that they will not contact each other during the movement of substrate 3 or during maintenance. However, the distance therebetween is preferably not more than approximately 100 mm to several 10 mm to maintain the measurement accuracy.

The film growth apparatus is, for example, a CVD (Chemical Vapor Deposition) apparatus that grows films in the unit of a plurality of films and placing the plurality of substrates with the grown film in respective trays. The plurality of substrates are stored in a load rock 14 provided in gate valve 13 of the unload chamber shown in FIG. 20B. A substrate transportation robot 11 takes out the substrate one by one from load rock 14 and places the substrate 3 on a robot hand 12. Robot 11 is moved so that substrate 3 is located right below sensor unit 50. When there are a plurality of measurement points in one substrate 3, robot 1 repeats movement of substrate 3 every time measurement of one measurement point ends so that the next measurement point is located right below sensor unit 50. Sensor unit 50 carries out thickness measurement of each measurement point every time substrate 3 is moved. The configuration of robot hand 12 is shown in FIG. 13C. Substrate 3 is often supported taking the shape of an inverted block upper case C-type symbol. Substrate 3 will droop by its own weight as a function of distance from the supported point. Substrate 3 may be slightly offset from the relative position by approximately several mm. Therefore, the thickness measurement apparatus must maintain the measurement accuracy with respect to such deviation and inclination.

The structure of sensor unit 50 will be described in detail hereinafter. Optical fiber 42B and optical fiber 42C described previously with reference to FIGS. 16 and 17 are provided at the leading end of sensor unit 50.

Although optical fiber 42B includes optical fibers 42BA and 42BB described above, optical fiber 42BA of FIG. 21 is formed of six optical fibers, arranged around optical fiber 42BB. Optical fiber 42BB and the six optical fibers 42BA have the same diameter. By this structure, optical fibers 42BB and 42BA can be set parallel to each other by arranging six optical fibers 42BA around optical fiber 42BB and fixing the optical fibers with jigs, as shown in FIG. 22. Therefore, assembly of optical fiber 42B is facilitated. Reflected light of light directed by any of the six optical fibers 42BA is received by optical fiber 42BB even if substrate 3 is inclined at the time of measuring the film thickness. Therefore, thin film thickness can be measured impervious to the inclination of substrate 3.

Figure 21:
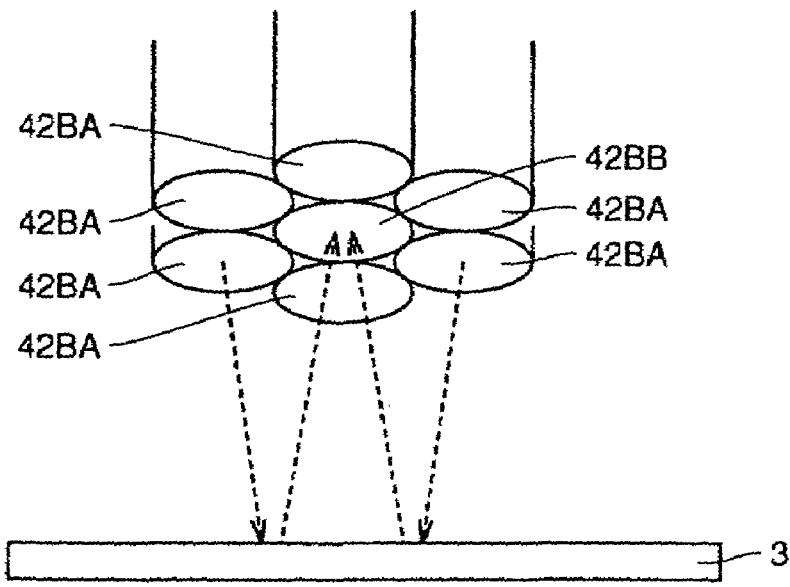
FIGS. 21 and 22 show a structure of optical fiber 42B.
Figure 22:
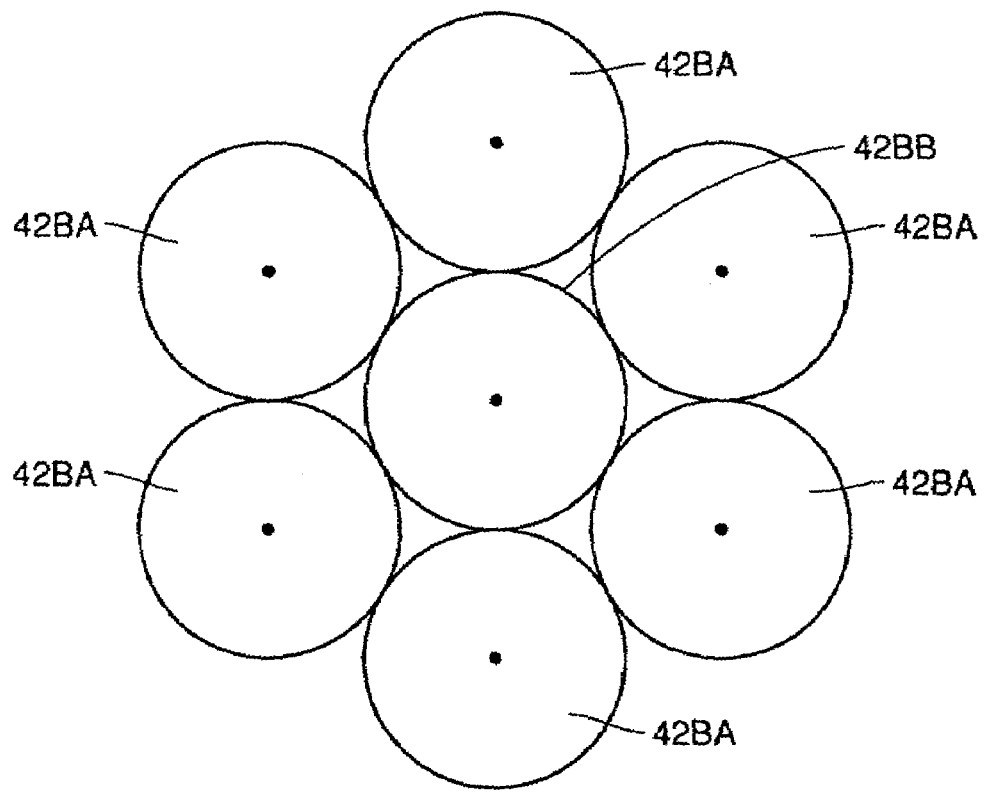

Optical fiber 42C is formed similar to that shown in FIG. 21.

The effect of vertical variation, inclination and oscillation of substrate 3 on measured values will be described with reference to FIGS. 14A, 23 and 24. It is assumed that the three layers of a GI layer, an i layer, and an $n^+$ layer are formed on the substrate. As previously described in the first embodiment with reference to FIG. 14A, respective layers in the multi layer structure in which a GI layer, an i layer and $n^+$ layer are deposited can be measured with almost no variation caused by the change of distance between sensor unit 10 and substrate 3. Although there is deviation of several mm in the distance between sensor unit 10 and substrate 3 by the warp of substrate 3, thin film thickness can be measured impervious thereto.

Figure 23:
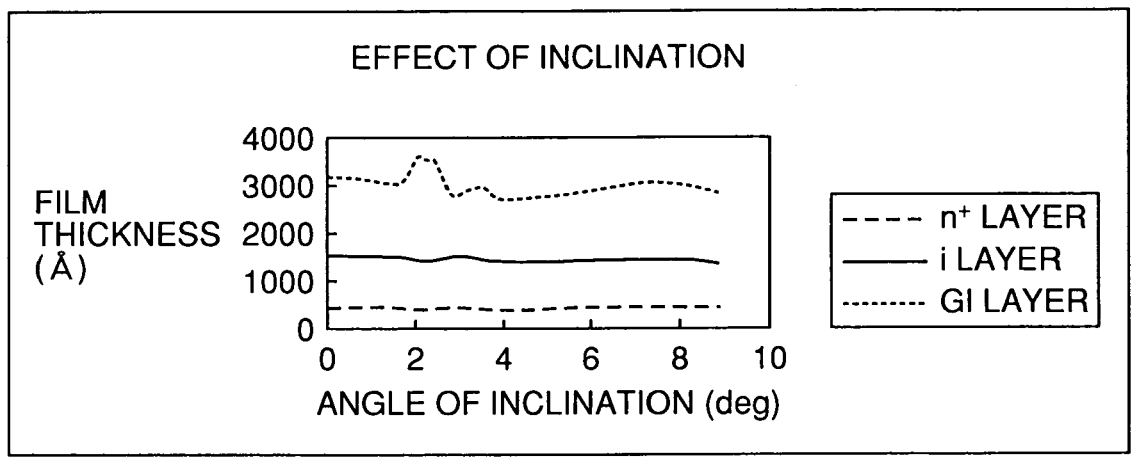
FIG. 23 is a graph representing the thin film thickness measurement result when the angle of inclination of the substrate is altered with respect to the sensor unit.

FIG. 23 is a graph in which the inclination angle of substrate 3 with respect to sensor unit 10 is plotted along the abscissa and the film thickness measured by the above-described film thickness measurement apparatus is plotted along the ordinate. When the inclination angle becomes 3–4° or more, the reflected light received becomes less than 50% that of the case where the inclination angle is 0°. However, it is appreciated from FIG. 13 that thin film thickness can be measured at a relatively high accuracy as long as the inclination of substrate 3 is not more than 8° (preferably, inclination of not more than 2°) in the multi layered structure in which the GI layer, i layer and $n^+$ layer are stacked.

Figure 24:
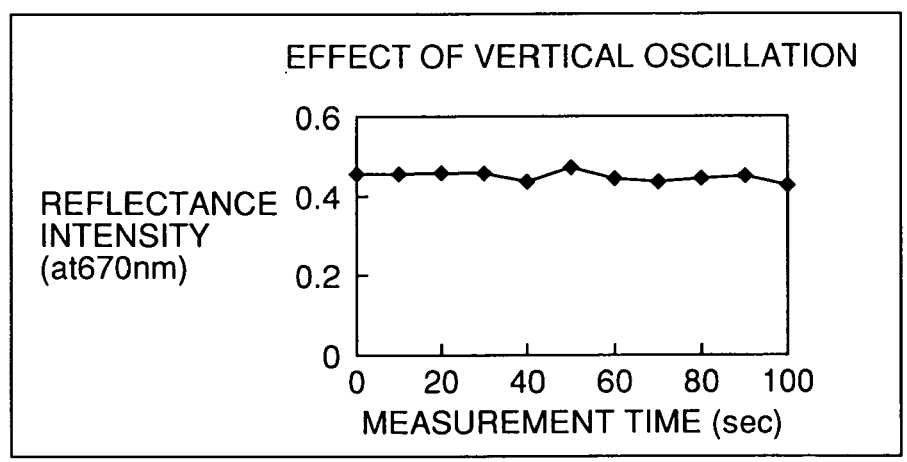
FIG. 24 is a graph representing the intensity of reflected light incident on the sensor unit over time when the substrate is oscillated vertically.

FIG. 24 represents a graph indicating the influence of vertical oscillation of substrate 3. The intensity of the reflected light is measured for every 10 seconds under the condition of a vertical amplitude of 4 mm and frequency of 5 Hz. The time of measurement is plotted along the abscissa and the reflectance intensity of the reflected light measured by the film thickness measurement apparatus is plotted along the ordinate. It is appreciated from FIG. 24 that the reflectance intensity is stable even when oscillation is imposed.

Figure 25:
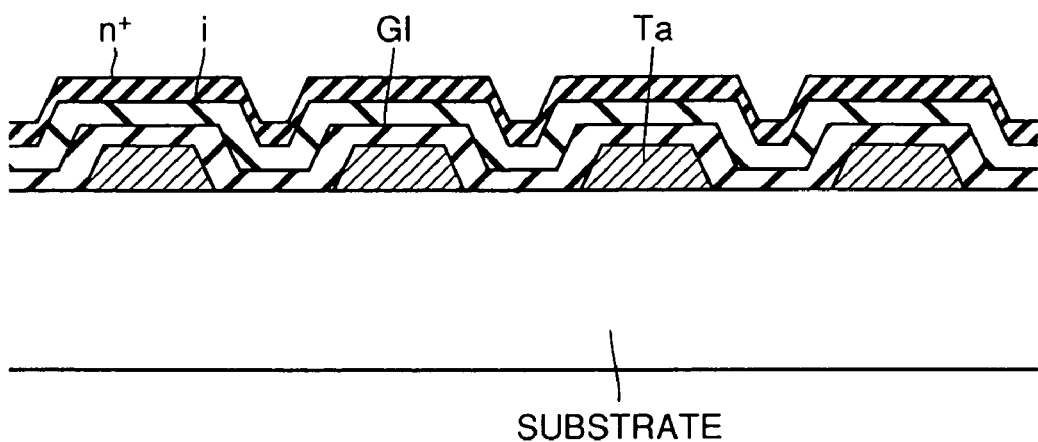
FIG. 25 shows a three layered structure of a GI layer, an i layer and an $n^+$ layer provided to cover a reflective film of Ta.
Figure 26:
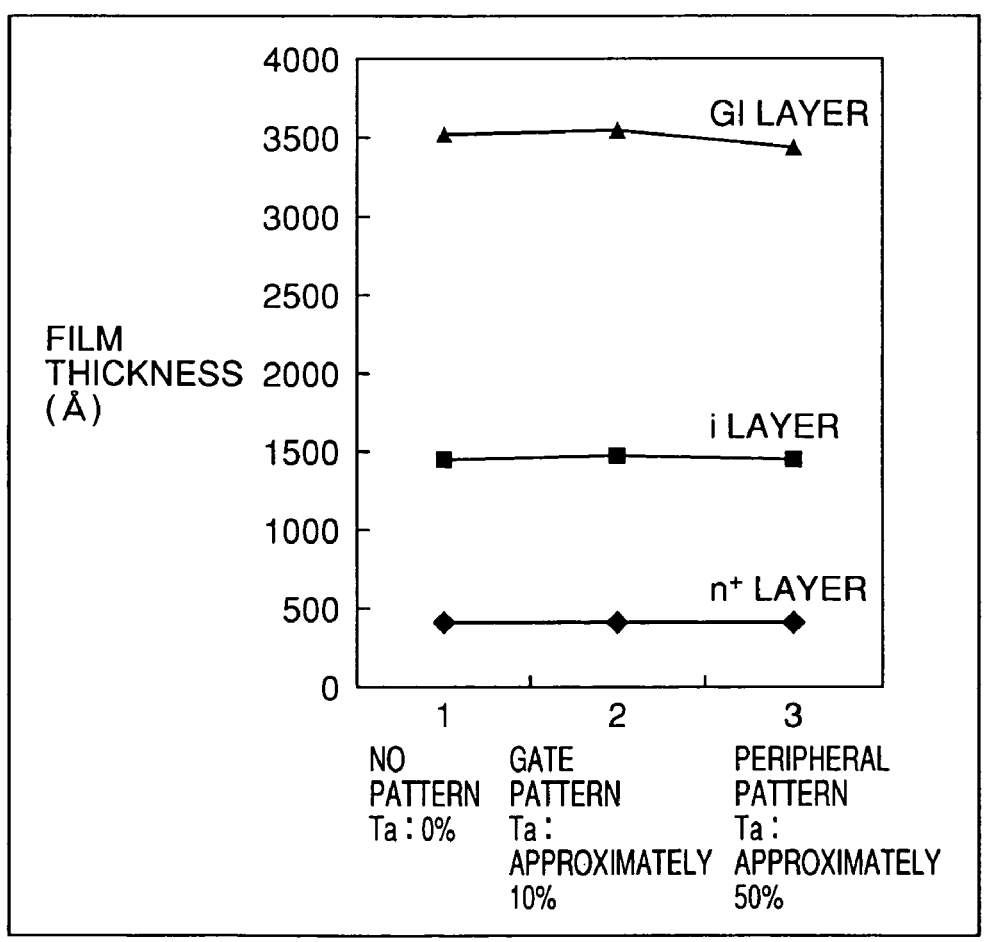
FIG. 26 is a graph representing the thin film thickness measurement result when the area ratio of the reflective film is altered.

The thickness is measured of each layer of the three layered structure in which a GI layer, i layer and $n^+$ layer are deposited so as to cover a reflective film of tantalum (Ta) as shown in FIG. 25. Film thickness measurement is carried out on the assumption that all the layers under the target layer is of a glass substrate. FIG. 26 shows the film thickness of the GI layer, i layer and $n^+$ layer in the region where there is no reflective film, inside the display portion of the liquid crystal display in which a reflective film is present approximately 10%, and around the display portion of the liquid crystal display in which a reflective film is present approximately 50%. The variation in the GI layer, i layer and $n^+$ layer is approximately ±2.5%, ±1.3% and ±1.0%, respectively. Therefore, the measurement result of the film thickness of each layer is stable. This is because influence of light refraction is reduced by directing light substantially perpendicular to substrate 3, whereby the effect of the direction of light reflectance altered at the edge of the reflective film is reduced.

The amount of light and wavelength distribution changes over time for the halogen lamp employed as light source 41 in obtaining the thickness of the thin film. Therefore, it is preferable to correct respective parameters by obtaining the spectrum of light emitted from light source 41 periodically using a total reflection substrate (such as a metal coat substrate) in obtaining reflected light intensity R.

Figure 27:
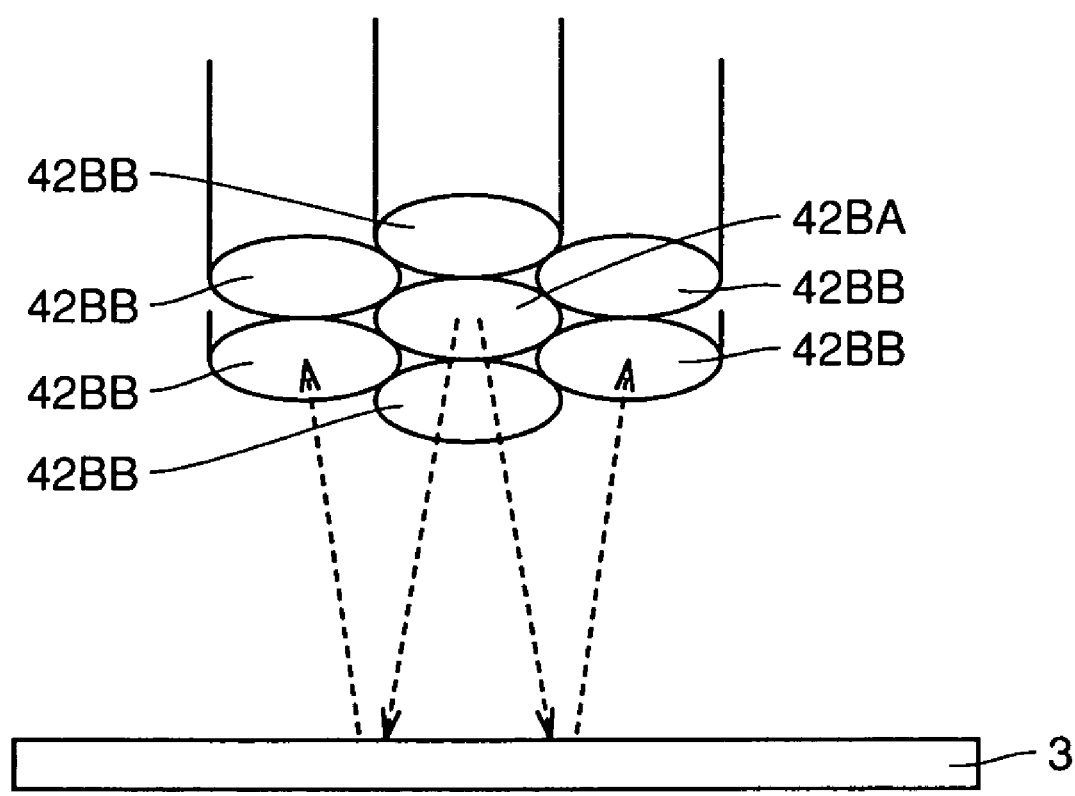
FIG. 27 shows a structure of optical fiber 42B.

As shown in FIG. 27, optical fiber 42B can be configured of six optical fibers 42BB arranged around an optical fiber 42BA having the same diameter. This structure provides the advantage that assembly of optical fiber 42B is facilitated. Reflected light of the light directed by optical fiber 42BA can be received at any of the six optical fibers 42BA even if substrate 3 is inclined when the film thickness is to be measured. Accordingly, thin film thickness measurement can be carried out impervious to inclination of substrate 3. Optical fiber 42C can have a similar structure.

Two optical fibers 42B and 42C are provided at the leading end of sensor unit 50. However, three or more optical fibers can be provided instead. Thin film thickness measurement is carried out at a plurality of measurement points by moving substrate 3 through robot 11. Thin film thickness measurement of a plurality of measurement points can be carried out by moving sensor unit 50 instead.

According to the thin film thickness measurement apparatus of the present invention, the structure of sensor unit 50 is extremely simple. Therefore, down-sizing is allowed.

In analyzing film thickness measurement, analysis can be carried out exclusively by the wavelength-light intensity curve. Accordingly, the thin film can be measured in a short time even for a multilayered film and in the case of multi-site measurement. Introduction of the film thickness measurement apparatus into the fabrication line is facilitated due to its compact size. The film thickness can be measured immediately after film growth since measurement is allowed in a short period of time. Therefore, the time lag from the generation of a defect during fabrication and upto detection thereof can be shortened to minimize the damage caused by defect generation.

By saving the film thickness data and analyzing the data, the lifetime of the film growth apparatus and film growth material, appropriate time for maintenance of the film growth apparatus, and the time to modify the film growth conditions and the like, can be predicted. Therefore, unexpected maintenance can be avoided to allow stable operation of the film growth apparatus.

Third Embodiment

Figure 28:
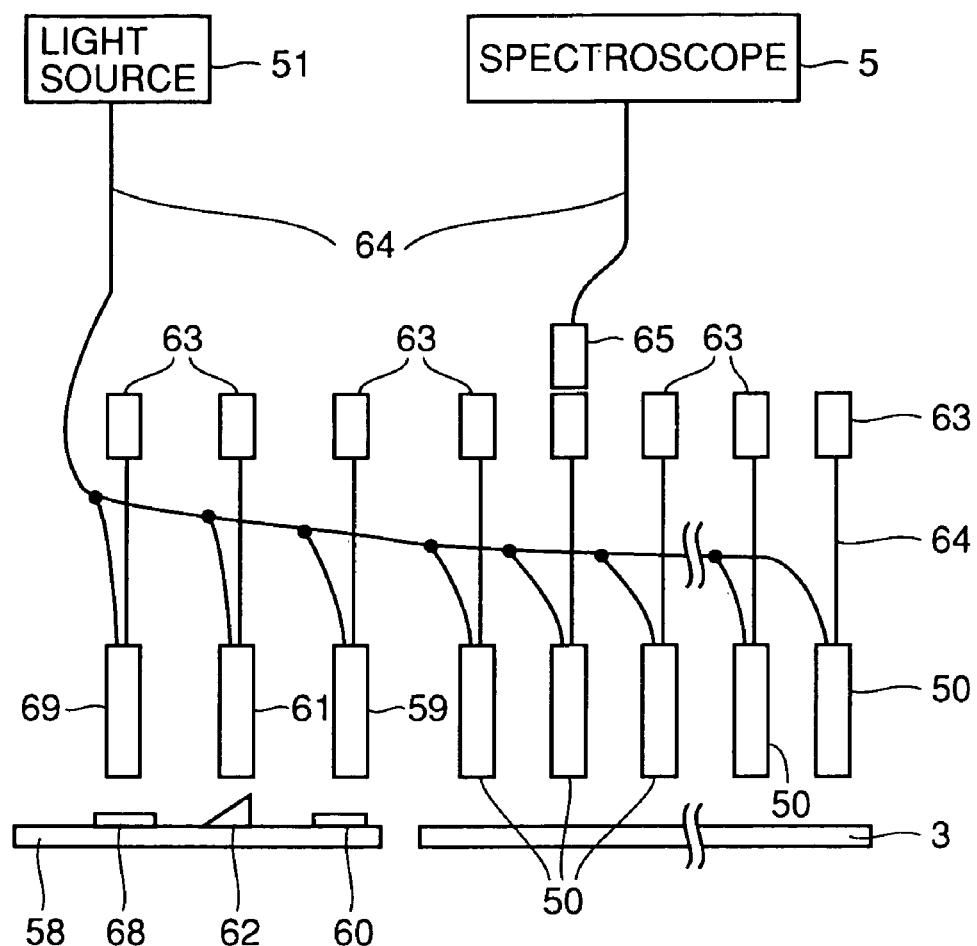
FIG. 28 is a block diagram to describe a structure of a thin film thickness measurement apparatus according to a third embodiment of the present invention.

Referring to FIG. 28, a thin film thickness measurement apparatus according to the third embodiment of the present invention includes a light source 51, a spectroscope 5, a plurality of sensor units 50 located opposite to substrate 3, a sensor unit 59 located opposite to calibration material 60 on a plate 58, a sensor unit 61 located opposite to a mirror 62 on plate 58, a sensor unit 69 located opposite to reflective material 68 on plate 58, a plurality of couplers 63 connected to the light receiving units of sensor units 50, 59, 61 and 69 via an optical fiber 64, a coupler 65 connected to spectroscope 5 via optical fiber 64, and connected to any of the plurality of couplers 63 to guide the light received at any of sensor units 50, 59, 61 and 69 to spectroscope 5, and a computer (not shown) connected to spectroscope 5 to analyze the light intensity for each wavelength to calculate the thin film thickness.

Calibration material 60 includes material that is subjected to mirror-polish and that has a known refractive index such as a silicon wafer. Mirror 62 is provided in a slanting manner to reflect the light emitted from sensor unit 61 outside sensor unit 61. Reflective material 68 corresponds to a total reflection substrate (such as a metal coat substrate).

Figure 29:
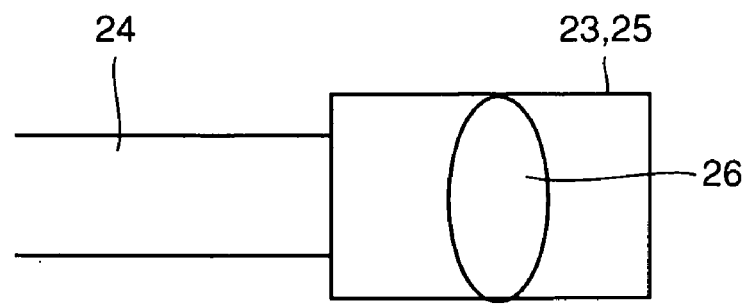
FIG. 29 is a sectional view showing a structure of a coupler.

Couplers 63 and 65 are connected to each other to function as a connector that connects optical fibers 64 with each to prevent light leakage. Referring to FIG. 29, a collective lens 66 are incorporated in couplers 63 and 65 to improve the light usage efficiency.

The computer computes the thin film thickness according to a method similar to that of computer 6 described with reference to the second embodiment. Therefore, details thereof will not be repeated. Spectroscope 5 is similar to that of the second embodiment. Therefore, details thereof will also not be repeated. Sensor units 50, 59, 61 and 69 have a structure similar to that of sensor unit 50 of the second embodiment. Therefore, details thereof will not be repeated. The details of optical source 51 will be described afterwards.

Figure 30:
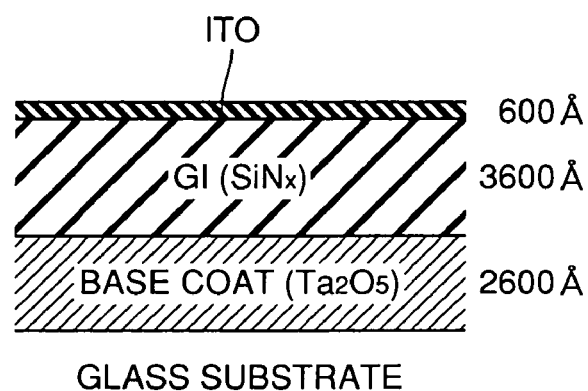
FIG. 30 is a sectional view of a pixel unit of a transmittive type liquid crystal display.

Measurement of the thickness of an ITO film which is a transparent conductive film having a thickness of not more than 100 nm (=1000 Å) will be described in the present embodiment. The ITO film generally employed in a liquid crystal display device is used as a pixel electrode. FIG. 30 shows a sectional view of the structure of the pixel portion of the transparent type liquid crystal display device. In such a structure, the property of the thin ITO film cannot be easily represented as the distribution of reflected light intensity. Therefore, it is difficult to measure the thickness of the ITO film by the evaluation method shown in the second embodiment.

Many liquid crystal display devices have a reflective film such as of Ta formed under the ITO film at the terminal unit that has a driver and the like mounted. The presence of a reflective film such of Ta as the underlying layer provides the advantage that distribution of reflected light intensity is stabilized to allow measurement of high accuracy at that region.

Figure 31:
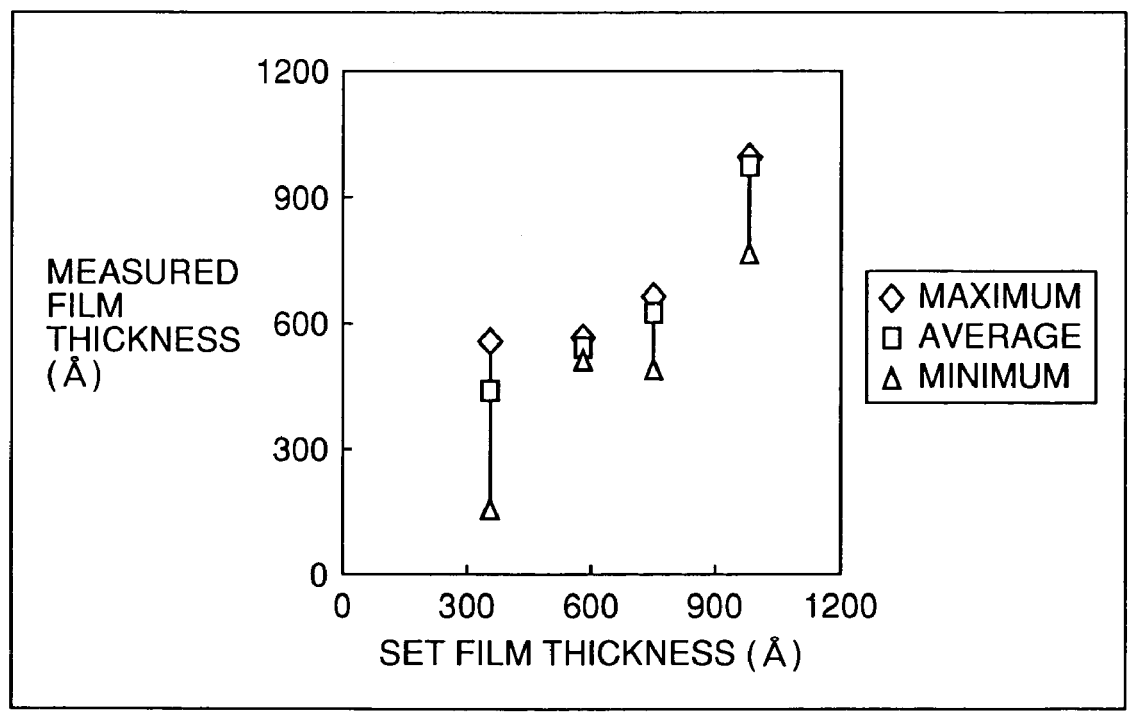
FIG. 31 is a graph representing the thickness measurement result of an ITO film when a halogen lamp is used as the light source.

FIG. 31 shows the result of measuring the thickness of an ITO film using a light source 41 formed of a halogen lamp (wavelength range approximately 400 nm-approximately 850 nm) similar to that of the second embodiment. The set film thickness of the production condition is plotted along the abscissa and the measured result by the film thickness measurement apparatus is plotted along the ordinate. The measured value of the film thickness is stable when the thickness of the thin film is 60 nm (=600 Å). However, variation in the measured value is great when the thickness of the ITO film is not 60 nm. It is therefore difficult to detect abnormal film thickness.

Figure 32:
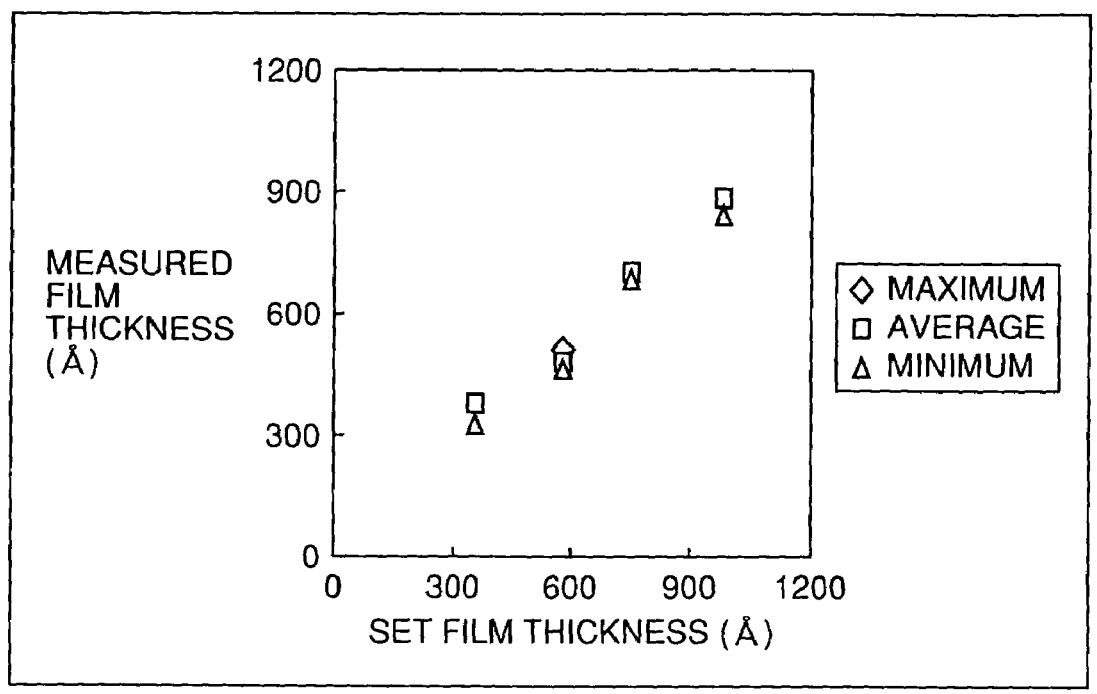
FIG. 32 is a graph representing the thickness measurement result of an ITO film when a halogen lamp and a deuterium lamp are employed as the light source.

Alternatively, the film thickness of an ITO film is measured using a halogen lamp and a deuterium lamp placed in the same light source chamber as light source 51 instead of light source 41, turned on at the same time (wavelength range approximately 220 nm-approximately 850 nm). FIG. 32 is a graph showing results thereof. It is appreciated from the graph of FIG. 32 that variation in the measured value is small in all the film thickness and that there is high correlation between the set film thickness under the production condition and the measured value. It is to be noted that there is a slight deviation between the set value of the film thickness and the measured value of the film thickness. This is attributed to a constant absorption coefficient k(p) set for each wavelength for the purpose of increasing the calculation speed. Therefore, if the relationship between the set value and the measured value of the film thickness is known in advance, accurate film thickness measurement is allowed by correcting the measured value of the film thickness. However, when abnormal film thickness is to be detected with the film thickness measurement apparatus employed in-line, only change over time of the film thickness at the measurement point is to be identified. The measured value correction is not required in such a case.

The computer calibrates various parameters and also detects reduction in the amount of light of light source 51 using sensor units 59, 61 and 69 when thin film thickness measurement is not carried out. When calibration is to be carried out using sensor unit 59, coupler 65 is connected to coupler 63 to which sensor unit 59 is connected. Light of a certain wavelength is emitted on calibration material 60. The light reflected from calibration material 60 is received by sensor unit 59. The computer calibrates various parameters by normalizing the dispersion the intensity of the received light. When calibration is to be carried out using sensor unit

61, the computer identifies the intensity of the disturbance light received at sensor unit 61 to calibrate various parameters so that influence of the disturbance light is eliminated.

When reduction of the light amount is to be detected using sensor unit 69, the computer monitors the intensity of light received at sensor unit 69. When the light intensity becomes lower than a predetermined value (for example, below 70% the initial intensity), reduction in the light amount of light source 51 is notified through a monitor (not shown) or the like. Reduction in the light amount of light source 51 can be detected using sensor unit 59 and calibration material 60 without the provision of sensor unit 69 and reflective material 68.

According to the thickness measurement apparatus of the present embodiment, film thickness measurement is carried out with respect to light in the wavelength range of approximately 220 nm-approximately 850 nm by using a light source 51 having a halogen lamp and a deuterium lamp turned on at the same time. In general, measurement must be carried out using light of a short wavelength in measuring the thickness of a thin film. By turning on a deuterium lamp at the same time, the thickness of the ITO film can be measured correctly than the case where only a halogen lamp is used.

Variation in the film thickness within the substrate is great when the substrate is of large size such as that employed in a liquid crystal display device. There is a possibility of local abnormal film growth due to abnormal discharge during film growth. By providing a plurality of sensor units, thickness measurement of a plurality of sites can be carried out simultaneously. Therefore, local film thickness error can be detected without degrading the production rate.

The light guided to the spectroscope is switched using a coupler. Therefore, light leakage is prevented to improve light usage efficiency in comparison to the case where a light restriction shutter is used. Accordingly, the accuracy of thin film thickness measurement can be improved.

Light leakage can further be prevented by the collective lens incorporated in the coupler. As a result, light usage efficiency is improved.

Various parameters are calibrated using the calibration material and mirror. Therefore, the thickness of a thin film can be measured while calibrating the parameter even during fabrication of a liquid crystal display device. Therefore, accuracy of thin film thickness measurement can be improved.

Reduction in the light amount of the light source is sensed using reflective material. Therefore, the lifetime of the light source can be identified in advance so that the light source can be exchanged prior to decay thereof. The operating efficiency of the thin film thickness measurement apparatus can be improved since replacement of the light source can be carried out during film growth or when the fabrication line is stopped.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A thin film thickness measurement apparatus comprising:
   a light source;
   a plurality of optical fibers for directing light from said light source substantially perpendicular to a substrate and for receiving light reflected from said substrate;
   an analyze unit for analyzing thickness of a thin film of said substrate according to intensity of reflected light received by said optical fibers, wherein
   (a) at least one of the optical fibers guides the light from said light source onto said substrate and receives light reflected from said substrate, and
   (b) at least one of the optical fibers guides the reflected light from said substrate to said analyze unit; and
   a shutter for selectively blocking the reflected light received by at least one of the optical fibers.

2. The thin film thickness measurement apparatus according to claim 1, said analyze unit including
   a spectroscope dividing reflected light from said substrate according to intensity of each wavelength, and
   a calculation unit calculating thickness of a thin film of said substrate according to intensity of each wavelength divided by said spectroscope.

3. The thin film thickness measurement apparatus according to claim 2, wherein said calculation unit calculates thickness of said thin film by equations of:

$$R = \frac{R(2,1) + R(1,0) \times k^2 + 2 \times \rho(2,1) \times \rho(1,0) \times k \times \cos(\gamma)}{1 + R(2,1) + R(1,0) \times k^2 + 2 \times \rho(2,1) \times \rho(1,0) \times k \times \cos(\gamma)}$$

$$\rho(2,1) = \frac{n_1 - n_2}{n_1 + n_2}$$

$$\rho(1,0) = \frac{n_0 - n_1}{n_0 + n_1}$$

$$R(2,1) = \rho(2,1)^2$$

$$R(1,0) = \rho(1,0)^2$$

$$\gamma = 4\pi n_1 d/\lambda$$

where $n_0$ is a refractive index of said substrate, $n_1$ is a refractive index of said thin film, $n_2$ is a refractive index of air, $\lambda$ is a wavelength of light, and k is an absorption coefficient of said thin film.

4. The thin film thickness measurement apparatus according to claim 3, wherein said plurality of optical fibers directs light substantially perpendicular to a substrate placed on a robot hand.

5. The thin film thickness measurement apparatus according to claim 3, wherein said plurality of optical fibers is installed in a neighborhood of an outlet of a gate valve of a film growth apparatus.

6. The thin film thickness measurement apparatus according to claim 2, wherein said calculation unit calculates thickness of said thin film by equations of:

$$R(p+1,0) = \frac{A+B}{1+C+B}$$

$$A = R(p+1,p) + R(p,0) \times k^2$$

$$B = 2 \times \rho(p+1,p) \times \sqrt{R(p,0)} \times k \times \cos(\gamma(p,0) + \gamma(p))$$

$$C = R(p+1,p) \times R(p,0) \times k^2$$

$$\rho(p+1,p) = \frac{n(p) - n(p+1)}{n(p) + n(p+1)}$$

$R(p+1,p)=\rho(p+1,p)^2$ $$\tan\gamma(p, 0) = \frac{D}{E+F}$$

$D=\sqrt{R(p-1,0)}\times(1-\rho(p,p-1)^2)\times\sin(\gamma(p-1,0)+\gamma(p-1))$ $E=\rho(p,p-1)\times(1+R(p-1,0))$ $F=\sqrt{R(p-1,0)}\times(1+\rho(p,p-1)^2)\times\cos(\gamma(p-1,0)+\gamma(p-1))$ $\gamma(p)=4\pi n(p)d(p)\cos\theta(p)/\lambda$ where $n_0$ is a refractive index of said substrate, $n(p)$ is a refractive index of the p-th layer of thin film from said substrate, $n(p+1)$ is a refractive index of air, $\lambda$ is a wavelength of light, and k is an absorption coefficient of said p-th layer of thin film.

7. The thin film thickness measurement apparatus according to claim 6, wherein said plurality of optical fibers directs light substantially perpendicular to a substrate placed on a robot hand.

8. The thin film thickness measurement apparatus according to claim 6, wherein said plurality of optical fibers is installed in a neighborhood of an outlet of a gate valve of a film growth apparatus.

9. The thin film thickness measurement apparatus according to claim 1, wherein said plurality of optical fibers directs lights substantially perpendicular to a substrate placed on a robot hand.

10. The thin film thickness measurement apparatus according to claim 1, wherein said light plurality of optical fibers is installed in a neighborhood of an outlet of a gate valve of a film growth apparatus.

11. A thin film thickness measurement method comprising the steps of:

providing a plurality of optical fibers;

directing light from a light source substantially perpendicular to a substrate via at least one of the optical fibers;

receiving light reflected from said substrate via at least one of the plurality of optical fibers;

utilizing a shutter to selectively block reflected light received by at least one of the optical fibers; and analyzing thickness of a thin film of said substrate according to intensity of said received reflected light to determine the thickness of the thin film during fabrication of the thin film to optimize fabrication yield and reliability of the thin film.

12. The thin film thickness measurement method according to claim 11, wherein said step of measuring thickness of said thin film includes the steps of dividing reflected light from said substrate according to intensity of each wavelength, and calculating thickness of a thin film of said substrate according to said intensity of each wavelength divided.

* * * * *